United States Patent
Zhang

(10) Patent No.: US 10,538,595 B2
(45) Date of Patent: Jan. 21, 2020

(54) MULTISPECIFIC ANTIBODY PLATFORM AND RELATED METHODS

(71) Applicant: BISON THERAPEUTICS INC., Princeton, NJ (US)

(72) Inventor: Wenjun Zhang, Princeton, NJ (US)

(73) Assignee: BISON THERAPEUTICS, INC., Princeton, NJ (US)

(*) Notice: Subject to any disclaimer, the term of this patent is extended or adjusted under 35 U.S.C. 154(b) by 176 days.

(21) Appl. No.: 15/542,781

(22) PCT Filed: Aug. 3, 2016

(86) PCT No.: PCT/US2016/045325
§ 371 (c)(1),
(2) Date: Jul. 11, 2017

(87) PCT Pub. No.: WO2017/034770
PCT Pub. Date: Mar. 2, 2017

(65) Prior Publication Data
US 2019/0119406 A1 Apr. 25, 2019

Related U.S. Application Data

(60) Provisional application No. 62/209,978, filed on Aug. 26, 2015.

(51) Int. Cl.
| | |
|---|---|
| *C07K 16/46* | (2006.01) |
| *C07K 16/28* | (2006.01) |
| *C07K 16/32* | (2006.01) |
| *A61K 47/64* | (2017.01) |
| *A61K 47/68* | (2017.01) |
| *C07K 16/06* | (2006.01) |

(52) U.S. Cl.
CPC .......... *C07K 16/468* (2013.01); *C07K 16/065* (2013.01); *C07K 16/2809* (2013.01); *C07K 16/32* (2013.01); *C07K 2317/14* (2013.01); *C07K 2317/21* (2013.01); *C07K 2317/24* (2013.01); *C07K 2317/31* (2013.01); *C07K 2317/526* (2013.01); *C07K 2317/53* (2013.01); *C07K 2317/622* (2013.01); *C07K 2317/92* (2013.01)

(58) Field of Classification Search
CPC ................ C07K 16/468; C07K 16/065; C07K 16/2809; C07K 16/2863; C07K 2317/526; C07K 2317/31; C07K 2317/622; C07K 2317/53; C07K 2317/92; C07K 2317/24; C07K 2319/00; C07K 2317/56; C07K 2317/52; C07K 16/46; C07K 16/00; C07K 2317/35; C07K 2317/55; C07K 2317/569; C07K 2319/35; C07K 2319/74; A61K 47/64; A61K 47/6803

See application file for complete search history.

(56) References Cited

U.S. PATENT DOCUMENTS

| | | | |
|---|---|---|---|
| 5,807,706 | A | 9/1998 | Carter et al. |
| 5,821,333 | A | 10/1998 | Carter et al. |
| 7,183,076 | B2 | 2/2007 | Arathoon et al. |
| 7,695,936 | B2 | 4/2010 | Carter et al. |
| 7,951,917 | B1 | 5/2011 | Aranthoon et al. |
| 8,216,805 | B2 | 7/2012 | Carter et al. |
| 8,592,562 | B2 | 11/2013 | Kanman et al. |
| 8,679,785 | B2 | 3/2014 | Carter et al. |
| 8,945,552 | B2 | 2/2015 | Baehner et al. |
| 9,017,686 | B2 | 4/2015 | Bostrom et al. |
| 2005/0136051 | A1 | 6/2005 | Scallon |
| 2005/0244403 | A1 | 11/2005 | Lazar et al. |
| 2009/0155275 | A1 | 6/2009 | Wu et al. |
| 2009/0182127 | A1 | 7/2009 | Kjaergaard et al. |
| 2009/0221803 | A1 | 9/2009 | Dall'Acqua et al. |
| 2010/0104564 | A1 | 4/2010 | Hansen et al. |
| 2010/0105873 | A1 | 4/2010 | Allan et al. |
| 2011/0054151 | A1 | 3/2011 | Lazar et al. |
| 2011/0077383 | A1 | 3/2011 | Dall'Acqua et al. |
| 2012/0116057 | A1 | 5/2012 | Kannan et al. |
| 2012/0283415 | A1 | 11/2012 | Humphreys et al. |
| 2013/0129723 | A1 | 5/2013 | Blankenship et al. |
| 2013/0253172 | A1 | 9/2013 | Gurney |
| 2014/0066599 | A2 | 3/2014 | Blein et al. |
| 2014/0170149 | A1 | 6/2014 | Nejissen et al. |
| 2014/0243505 | A1 | 8/2014 | Zhou et al. |

(Continued)

FOREIGN PATENT DOCUMENTS

| | | |
|---|---|---|
| WO | 2006104898 | 10/2006 |
| WO | 2007147901 | 12/2007 |

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Rudikoff et al., PNAS 79: 1979-1983 (Year: 1982).*
"Antibody." Wikipedia, Wikimedia Foundation, Accessed on Oct. 25, 2017, en.wikipedia.org/wiki/Antibody.
Molecular Cancer Therapeutics; Hye-Ji Choi, Ye-Jin Kim, Sangho Lee, and Yong-Sung Kim; A Heterodimeric Fc-Based Bispecific Antibody Simultaneously Targeting VEGFR-2 and Met Exhibits Potent Antitumor Activity; 12(12) Dec. 2013.

(Continued)

*Primary Examiner* — Phuong Huynh
(74) *Attorney, Agent, or Firm* — Gearhart Law, LLC

(57) ABSTRACT

Novel multispecific antibody platform, multispecific antibodies and a method to make the antibodies is disclosed here. The CH3 domain harboring polypeptide chains of the Fc-regions are modified by increasing the positive charge of one chain and negative charge of another chain. Heterodimer formation in cotransfection with the modified chains is comparable to formation of wild type antibodies when same cell line is transfected with wild type polypeptides. Moreover, the modification provides a simple one step purification of the heterodimers.

12 Claims, 13 Drawing Sheets
Specification includes a Sequence Listing.

(56) References Cited

U.S. PATENT DOCUMENTS

2014/0294759 A1   10/2014   Chu et al.
2014/0308285 A1   10/2014   Yan et al.
2014/0336361 A1   11/2014   Giese et al.
2014/0348839 A1   11/2014   Chowdhury et al.
2014/0377270 A1   12/2014   Moore et al.
2015/0119555 A1    4/2015   Jung et al.

OTHER PUBLICATIONS

Journal of Biological Chemistry; Kannan Gunasekaran, Martin Pentony, Min Shen, Logan Garrett, Carla Forte, Anne Woodward, Soo Bin Ng, Teresa Born, Marc Retter, Kathy Manchulenko, Heather Sweet, Ian N. Foltz, Michael Wittekind, and Wei Yan; Enhancing Antibody Fc Heterodimer Formation through Electrostatic Steering Effects;vol. 285, No. 25, pp. 19637-19646, Jun. 18, 2010.

Acta Pharmacologica Sinica;Jonathan S Marvin, and Zhenping Zhu; Recombinant approaches to IgG-like bispecific antibodies; Jun. 2005; 26 (6): 649-658.

PCT International Search Report; PCT/US2016/045325, dated Nov. 23, 2016, 4 Pages.

PCT Notification of Written Opinion; PCT/US2016/045325, dated Nov. 23, 2016, 6 Pages.

PNAS; M. J. Nohaile, Z. S. Hendsch, B. Tidor, and R. T. Sauer; Altering dimerization specificity by changes in surface electrostatics; vol. 98, No. 6, Mar. 13, 2001.

Protein Engineering; Zhuang Zuo, Xenia Jimenez, Larry Witte, and Zhenping Zhu; An efficient route to the production of an IgG-like bispecific antibody; vol. 13, No. 5, Accepted, Feb. 20, 2000.

\* cited by examiner

FIG. 1A

SEQUENCE LISTING

<160> NUMBER OF SEQ ID NOS: 36

<210> SEQ ID NO 1
<211> LENGTH: 13
<212> TYPE: PRT
<213> ORGANISM: Artificial Sequence
<220> FEATURE:
<221> NAME/KEY: misc_feature
<222> LOCATION: (1)..(13)
<223> OTHER INFORMATION: synthesized

<400> SEQUENCE: 1

Ser Asp Lys Thr Glu Pro Cys Gly Glu Cys Pro Ala Pro
1               5                   10

<210> SEQ ID NO 2
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: chemically synthesized

<400> SEQUENCE: 2
tctgacaaaa ctgaaccctg cggagaatgc ccagcacct                    39

<210> SEQ ID NO 3
<211> LENGTH: 12
<212> TYPE: PRT
<213> ORGANISM: Artificial Sequence
<220> FEATURE:
<221> NAME/KEY: misc_feature
<222> LOCATION: (1)..(12)
<223> OTHER INFORMATION: synthesized

<400> SEQUENCE: 3

Asp Lys Thr His Arg Cys Lys Ser Cys Pro Ala Pro
1               5                   10

<210> SEQ ID NO 4
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: chemically synthesized

```
<400> SEQUENCE: 4
gacaaaactc accgatgcaa atcctgccca gcacct                                36

<210> SEQ ID NO 5
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized

<400> SEQUENCE: 5

Tyr Lys Thr Thr Lys Lys Lys Leu Asp Ser Asp
1               5                   10

<210> SEQ ID NO 6
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: chemically synthesized

<400> SEQUENCE: 6
tacaagacca cgaagaagaa gctggactcc gac                                   33

<210> SEQ ID NO 7
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized

<400> SEQUENCE: 7

Tyr Lys Thr Asp Asp Asp Val Leu Asp Ser Asp
1               5                   10

<210> SEQ ID NO 8
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: chemically synthesized

<400> SEQUENCE: 8
tacaagaccg atgacgatgt gctggactcc gac                                   33

<210> SEQ ID NO 9
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized

<400> SEQUENCE: 9

Tyr Lys Thr Thr Lys Lys Cys Leu Asp Ser Asp
1               5                   10

<210> SEQ ID NO 10
```

-continued

```
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: chemically synthesized

<400> SEQUENCE: 10
tacaagacca cgaagaagtg cctggactcc gac                            33

<210> SEQ ID NO 11
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized

<400> SEQUENCE: 11

Tyr Lys Thr Cys Asp Asp Val Leu Asp Ser Asp
1               5                   10

<210> SEQ ID NO 12
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: chemically synthesized

<400> SEQUENCE: 12
tacaagacct gcgacgatgt gctggactcc gac                            33

<210> SEQ ID NO 13
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized

<400> SEQUENCE: 13

Tyr Lys Thr Thr Arg Arg Arg Leu Asp Ser Asp
1               5                   10

<210> SEQ ID NO 14
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: chemically synthesized

<400> SEQUENCE: 14
tacaagacca cgagacgaag gctggactcc gac                            33

<210> SEQ ID NO 15
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized
```

<400> SEQUENCE: 15

Asn Tyr Lys Thr Glu Glu Glu Val Leu Asp Ser
1               5                   10

<210> SEQ ID NO 16
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: chemically synthesized

<400> SEQUENCE: 16
aactacaaga ccgaagagga agtgctggac tcc                                33

<210> SEQ ID NO 17
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized

<400> SEQUENCE: 17

Asn Asn Tyr Lys Lys Lys Lys Pro Val Leu Asp
1               5                   10

<210> SEQ ID NO 18
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: chemically synthesized

<400> SEQUENCE: 18
aacaactaca agaagaagaa gcccgtgctg gac                                33

<210> SEQ ID NO 19
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized

<400> SEQUENCE: 19

Lys Thr Thr Pro Asp Asp Asp Asp Ser Asp Gly
1               5                   10

<210> SEQ ID NO 20
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: chemically synthesized

<400> SEQUENCE: 20
aagaccacgc ctgacgatga cgactccgac ggc                                33

```
<210> SEQ ID NO 21
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized

<400> SEQUENCE: 21

Asn Tyr Lys Thr Lys Lys Lys Val Leu Asp Ser
1               5                   10

<210> SEQ ID NO 22
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: chemically synthesized

<400> SEQUENCE: 22
aactacaaga ccaagaaaaa ggtgctggac tcc                                   33

<210> SEQ ID NO 23
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized

<400> SEQUENCE: 23

Tyr Lys Thr Thr Asp Asp Asp Leu Asp Ser Asp
1               5                   10

<210> SEQ ID NO 24
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: chemically synthesized

<400> SEQUENCE: 24
tacaagacca cggatgacga cctggactcc gac                                   33

<210> SEQ ID NO 25
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized

<400> SEQUENCE: 25

Lys Thr Thr Pro Lys Lys Lys Asp Ser Asp Gly
1               5                   10

<210> SEQ ID NO 26
<211> LENGTH: 33
<212> TYPE: DNA
<213> ORGANISM: Artificial Sequence
<220> FEATURE:
<221> NAME/KEY: misc_feature
```

```
<222> LOCATION: (1)..(33)
<223> OTHER INFORMATION: chemically synthesized

<400> SEQUENCE: 26
aagaccacgc ctaagaaaaa ggactccgac ggc                                33

<210> SEQ ID NO 27
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized

<400> SEQUENCE: 27

Asn Asn Tyr Lys Asp Asp Asp Pro Val Leu Asp
1               5                   10

<210> SEQ ID NO 28
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: chemically synthesized

<400> SEQUENCE: 28
aacaactaca aggacgacga ccccgtgctg gac                                33

<210> SEQ ID NO 29
<211> LENGTH: 13
<212> TYPE: PRT
<213> ORGANISM: Artificial Sequence
<220> FEATURE:
<221> NAME/KEY: misc_feature
<222> LOCATION: (1)..(13)
<223> OTHER INFORMATION: synthesized

<400> SEQUENCE: 29

Asp Gly Ser Phe Glu Leu Glu Ser Glu Leu Thr Val Asp
1               5                   10

<210> SEQ ID NO 30
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: chemically synthesized

<400> SEQUENCE: 30
gacggctcct tcgaactcga aagcgaactc accgtggac                          39

<210> SEQ ID NO 31
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized

<400> SEQUENCE: 31

Asp Gly Ser Phe Lys Leu Lys Ser Lys Leu Thr
1               5                   10
```

```
<210> SEQ ID NO 32
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: chemically synthesized

<400> SEQUENCE: 32
gacggctcct tcaaactcaa gagcaagctc acc                         33

<210> SEQ ID NO 33
<211> LENGTH: 10
<212> TYPE: PRT
<213> ORGANISM: Artificial Sequence
<220> FEATURE:
<221> NAME/KEY: misc_feature
<222> LOCATION: (1)..(10)
<223> OTHER INFORMATION: synthesized

<400> SEQUENCE: 33

Thr Leu Pro Pro Asp Asp Glu Glu Met Thr
1               5                   10

<210> SEQ ID NO 34
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: chemically synthesized

<400> SEQUENCE: 34
accctgcccc cagacgatga ggagatgacc                             30

<210> SEQ ID NO 35
<211> LENGTH: 11
<212> TYPE: PRT
<213> ORGANISM: Artificial Sequence
<220> FEATURE:
<221> NAME/KEY: misc_feature
<222> LOCATION: (1)..(11)
<223> OTHER INFORMATION: synthesized

<400> SEQUENCE: 35

Arg Glu Pro Gln Lys Lys Lys Leu Pro Pro Ser
1               5                   10

<210> SEQ ID NO 36
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: chemically synthesized

<400> SEQUENCE: 36
cgagaaccac agaagaagaa gctgccccca tcc                         33
```

MULTISPECIFIC ANTIBODY PLATFORM AND RELATED METHODS

PRIORITY

This application is a national application of the international application number PCT/US2016/045325 which was filed on Aug. 3, 2016 and which claimed priority of US provisional application number U.S. 62/209,978 having a filing day of Aug. 26, 2015. This application claims priority of both of these applications and the contents of both of them are incorporated herein by reference in their entirety.

SEQUENCE LISTING

This application contains sequence data.

FIELD OF THE INVENTION

The invention relates to multispecific antibody platform, multispecific antibodies, including bispecific antibodies, and methods for producing them.

BACKGROUND OF THE INVENTION

Antibodies are large glycoproteins, secreted by B-lymphocyte derived plasma cells in response to an antigen. There are five major classes of antibodies: IgG, IgM, IgA, IgE, and IgD. IgG represents about 75% of serum antibodies in human body and it is the most common type of antibody found in the circulation. In all the five major classes of antibodies the basic unit is a Y-shaped monomer, which consists of two identical heavy chains (HC) and two identical light chains (LC). Each LC has one variable domain (VL) and one constant domain (CL). Each HC has one variable domain (VH) and three constant domains (CH). The 'arms' in the Y-structure form the antigen binding fragment (Fab). The arms are connected by a flexible hinge region to homodimeric Fc fragment (Fragment crystallizable) which forms the 'base' of the Y structure. The ability of an antibody to communicate with the other components of the immune system is mediated via the Fc-region. Production of homodimeric Fc-regions in mammalian cell lines is known in the art. Such homodimeric Fc regions may be used for example to bring antibody like qualities to fusion proteins.

A bispecific antibody (BsAb) is an artificial protein that is composed of fragments of two different antibodies and consequently BsAb binds to two different types of antigens. Bispecific antibodies belong to multispecific antibodies. Multispecific antibodies may be bispecific, trispecific, or quardo-specific antibodies. The Fc-fragments of such multispecific antibodies are preferably heterodimers. Bispecific, as well as other multispecific antibodies in general have shown tremendous potential in a broad range of clinical and diagnostic applications. There are two bispecific antibody drugs approved in European Union and in the US for treatment of oncological diseases (Catumaxomab and Blinatumab). Due to their unique features, bispecific and multispecific antibodies generally have staged to be a very attractive format for next generation of antibody therapeutics.

In the clinical research area, diagnostic applications for specific antibodies have been described in several publications (e.g. Fanger et al. Crit. Rev. Immunol. 1992, 12:101-124; Nolan, et al. Biochem. Biophys. Acta. 1990, 1040:1-11; Song-Sivilai et al. Clin Exp. Immunol. 1990, 79:315). However, the most impressive application for bispecific antibodies (BsAb) reside in immune-oncology field. Theoretically, one arm of BsAb can bind to a tumor antigen on the tumor cells, and the second arm of the BsAb can bind to an immune effector cell marker. Thus, BsAbs can serve as a bridging agent to recruit immune effector cells (natural killer cells or effector T-cells) and bring them to the local tumor site to kill tumor cells. Those therapeutic applications have been described in numerous publications (Hseih-Ma et al., Cancer Res. 1992, 52:6832-6839; Weiner et al., Cancer Res. 1993, 53: 94-100; Shalaby et al. J. Exp. Med. 1992, 175: 217; Weiner et al., J. Immunol. 1994, 152:2385).

Several different ways to make BsAbs or multispecific antibodies are known in the art. In the 1980's, bispecific antibodies were generated by cross-hybrid of two different hybridomas (Millstein and Cello, Nature 1983, 305: 537-539). Because of the random pairing of two different heavy chains and two different light chains, those hybrid hybridomas (also called quadromas) could generate up to 10 different kinds of antibody combinations, only one of which was the desired BsAb-format. This situation resulted in cumbersome and low yield purification of the correct BsAb-format. To overcome the random assortment problems, it is preferred to create two differently modified Fc-domains such that those two modified Fc domains are able to favor heterodimerc formation over homodimeric formation when they meet each other. Each modified Fc can be fused with a Fab or ScFv with a unique binding specificity. When those two differently modified Fc containing fragments with different binding specificities are co-expressed in a mammalian cell culture, they can form a heterodimeric bispecific antibody with a favorable yield.

Another approach is disclosed in PCT patent application publication WO2007/147901 and in U.S. Pat. No. 8,592,562, in which the electric charges of the first CH3 domain and the second CH3 domain are re-distributed such that those two differently modified CH3 domains will favor heterodimer formation over homodimer formation. However, generally, co-expressing two different Fc heavy chains in mammalian cells may result to formation of some heterodimeric Fc fragments, but also to substantial formation of homodimeric fragments. Purification of the heterodimeric fragments from the co-transfected cell culture or engineered stable cell line supernatant is cumbersome and expensive.

Certain improvements have been introduced to this problem. U.S. Pat. No. 5,807,706 for example, discloses so called 'knob-into-hole' mutations at the CH3 domain. By employing the 'knob into hole" strategy, several other methods have been disclosed for example in US patent applications 2014/0348839 and 2013/0245233). This technology resulted in higher formation of heterodimers, but some 'hole' homodimers and 'knob' monomers were still present. US patent application number 2012/0116057 disclosed an improvement in heterodimerization by substituting serine at position of 364 preferably with alanine in the wild type CH3 domain. Such substitution led to increased aggregation of heterodimeric Fc.

Antibodies have become increasingly important in developing therapeutic compositions. Multispecific antibody derivatives, including bispecific antibodies may be considered as the next generation of targeted biologics for cancer therapy. Multispecific antibodies bind at least two antigens or epitopes. Application of multispecific antibodies in experimental cancer therapy includes molecules that bind different cell surface proteins to achieve more complete blockage of proliferative or angiogenesis-associated pathways. Multispecific antibodies can also be applied as vehicles to deliver immune effector cells to tumors. Accordingly, multispecific antibodies are desirable due to their capability to bind more than one antigen. However, making and purifying multispecific antibodies, including bispecific antibodies, is still technical challenge and also very expensive. Therefore, new methods are required to make such antibodies with high purity.

Various implements are known in the art, but fail to address all of the problems solved by the invention described herein. One embodiment of this invention is illustrated in the accompanying drawings and will be described in more detail herein below.

SUMMARY OF THE INVENTION

The present invention succeeds in conferring the following, and others not mentioned, desirable and useful benefits and objectives. The invention described herein provides a platform for new multispecific antibodies, including bispecific antibodies, new antibodies and antibody derivatives, new methods to provide the antibodies and new methods to provide highly purified new multispecific antibodies.

The present invention provides a novel bi- or multispecific antibody platform to enhance heterodimerization of two differently modified mammalian IgG Fc-regions as well as IgA, IgD, IgE and IgM Fc regions. The invention also provides optional modifications in the hinge region. The invention further provides a simplified one-step purification to achieve high purity of heterodimers.

It is an object of this invention to provide a strategy for modifying antibody CH3 domain to engineer the interface between a first CH3-harboring polypeptide and a second CH3-harboring polypeptide for heterodimerization. In particular, at least two, preferably two to six and most preferably, three to four positively charged amino acids, such as, but not limited to, arginine, lysine or histidine, are introduced to the interface of the first polypeptide by amino acid substitution to increase the positive charge. At the same time, at least two, preferably two to six and most preferably, three to four negatively charged amino acids, such as, but not limited to, aspartic acid or glutamic acid, are introduced to the complementary interface of the second polypeptide by amino acid substitution to increase negative charges of the polypeptide chain. Those different modifications at the interface of two complementary CH3 domains presumably provide much stronger electrostatic attractions between those two chains to favor heterodimer formation rather than homodimer formation. In addition, cysteine molecules may be introduced together with charged amino acids to the appropriate position of both interfaces of the two complementary CH3 domains to allow inter-chain disulfide bond formation and further strengthen the heterodimer formation.

It is another object of the present invention to provide a method of generating such amino acid substitutions so that the introduced positively charged amino acids on the first polypeptide chain will reside at the most appropriately oriented positions that interact with the opposite negatively charged amino acids at the closest proximity position of the complementary interface of the second polypeptide chain. When those amino acid substitutions are positioned properly, the heterodimer formation is electrostatically favorable: e.g. opposite charges are in the closest proximity positions of interfaces of two paring CH3 domains.

Yet another object of the present invention is to provide a method for preparing a heterodimeric antibody, which may be bispecific or multispecific binding protein. The heterodimeric antibody may comprise a first modified CH3 harboring polypeptide and a second modified CH3 harboring polypeptide that meet at an interface and come together to enhance heterodimer formation. In certain aspects, the molecule may be a bispecific, trispecific or quadrospecific antibody. The N-terminus of the first CH3-containing polypeptide can be fused with a heavy chain Fab region (VH and CH1), a ScFv, a probody, monobody, diabody, nanobody, a ligand or receptor or any kind of binding domains. The C terminus of the first CH3 containing polypeptide may be fused with a different heavy chain Fab region (VH and CH1), a ScFv, a probody, monobody, diabody, nanobody, a ligand or receptor or any kind of binding domains. A peptide linker may be used in between the fused binding unit and the first polypeptide chain. At the same time, the N-terminus of the second CH3 domain containing polypeptide may be fused with yet another different heavy chain Fab region (VH and CH1), a ScFv, a probody, monobody, diabody, nanobody, a ligand or receptor or any kind of binding domains. The C-terminus of said second CH3 containing polypeptide may be fused with yet another different heavy chain Fab region (VH and CH1), a ScFv, a probody, monobody, diabody, nanobody, a ligand or receptor fusions or any form of mini-binding domains. A peptide linker may be introduced in between the fused binding unit and said second chain.

Still another object of the present invention is to provide a method to produce such heterodimeric proteins using a transient transfected cell culture system, a stably engineered cell line system or an in vitro cell-free protein synthesis system. Those systems comprise nucleic acids that encode the first chain and the second chain. Those two chains can be encoded on the same vector or on two separate vectors. The cell culture systems that may be used include, but not limited to mammalian cell (e.g. CHO, HEK293 or myeloma NS0 cells), insect cell, yeast cell or bacterial cell system. In certain embodiments, the ratio between nucleic acids encoding the first CH3 harboring polypeptide and the second CH3 harboring polypeptide can vary from 1:2 to ratios other than 2:1. In a preferred embodiment, 1:1 ratio is used.

Still another object of the present invention is a method to purify said heterodimeric proteins. The standard monoclonal antibody purification techniques can be used to purify the heterodimeric antibodies. Those techniques include, but are not limited to protein A affinity chromatography, size exclusion and ion exchange chromatograph, as well as ammonium precipitation.

In a preferred embodiment, a negatively charged amino acid substituted second polypeptide lost almost all its protein A binding property coincidently. This unique feature provides a technical advantage for purification of said heterodimeric protein. Because only the first polypeptide in the heterodimeric antibody binds to Protein A, and the second polypeptide does not bind, therefore the heterodimer has low binding affinity to protein A column and can be eluted at higher pH compared to normal Fc homodimer with two chain binding to protein A. The molecule generated from the present invention can be eluted at pH 4 while the homodimer still retains on the protein A column.

In certain embodiments, the CH3 containing polypeptides can be immunoglobulin molecules from, but not limited to human, mouse, bovine, horse, chicken, rat, non-human primates, camel, Llama, Alpaca, guanaco, vicunas or shark. Yet in other aspects, the immunoglobulin can be IgG, IgA, IgM, IgE and IgD or their subtypes (eg. IgG1, IgG2, IgG3 or IgG4 etc.). The CH3 domain containing polypeptide may contain additional alterations, such as non-natural amino acids, Fc effector function mutations and glycosylation site mutations.

Yet another aspect of the present invention is that the said heterodimeric antibodies may be used as pharmaceutical or therapeutic compositions. The heterodimeric proteins can be formulated in a composition that contains other pharmaceutical acceptable buffers, ingredients or excipients. Such pharmaceutical composition may be administrated to a patient to treat a disease or prevent a disease.

Still another object of the present invention is to provide a molecule comprising a pair of antibody fragments, each of which contains a modified CH3 domain to facilitate heterodimeric formation. In one aspect, the molecule has substantially the same yield as wild type antibody Fc when expressed in a comparable expression system. In another further aspect, the modified CH3 domain from the first fragment of the said molecule contains 3 or 4 amino acid substitutions preferred at the edge interface, at least two, preferably two to six and most preferably three to four, of which had been changed to positively charged amino acid selected from arginine, histidine or lysine. One amino acid may be changed to a positively charged amino acid, a cysteine or other non-charged amino acid. Yet in another aspect, the modified CH3 domain from the second fragment of the molecule contains 3 or 4 amino acid substitutions preferred at the edge interface, at least two, preferably two to six and most preferably three to four, of which have been changed to negatively charged amino acid selected from aspartic acid or glutamic acid. One amino acid may be changed to a negatively charged amino acid, a cysteine or other non-charged amino acid.

It is an object of this invention to provide a multispecific heterodimeric antibody molecule comprising a first immunoglobulin heavy chain and a second immunoglobulin heavy chain, wherein CH3 domain of the first heavy chain comprises at least two, preferably two to six and most preferably three to four, amino acid mutations, and CH3 domain of the second heavy chain comprises at least two, preferably two to six and most preferably three to four, amino acid mutations, wherein the at least two, preferably two to six and most preferably three to four, mutations in the first heavy chain CH3 domain are mutated to two, preferably two to six and most preferably three to four, positively charged amino acids, and the at least two, preferably two to six and most preferably three to four, mutations in the CH3 domain of the second heavy chain are mutated to two, preferably two to six and most preferably three to four, negatively charged amino acids, and wherein each mutation locate in edge interface from Y391 to S400, edge interface Q 347 to E357 or in middle interface from D401 to L410.

It is an object of this invention to provide a multispecific heterodimeric antibody molecule comprising a first immunoglobulin heavy chain and a second immunoglobulin heavy chain, wherein CH3 domain of the first heavy chain comprises at least two, preferably two to six and most preferably three to four, amino acid mutations, and CH3 domain of the second heavy chain comprises at least two, preferably two to six and most preferably three to four, amino acid mutations, wherein the at least two, preferably two to six and most preferably three to four, mutations in the first heavy chain CH3 domain are mutated to two, preferably two to six and most preferably three to four, positively charged amino acids, and the at least two, preferably two to six and most preferably three to four, mutations in the CH3 domain of the second heavy chain are mutated to two, preferably two to six and most preferably three to four, negatively charged amino acids, wherein the substitutions in the CH3 domain of the first heavy chain are selected from the group consisting of Y391K, Y391R, Y391H, K392R, K392H, T393K, T393R, T393H, T394K, T394R, T394H, P395K, P395R, P395H, P396K, P396R, P396H, V397K, V397R, V397H, V397C, L398K, L398R, L398H, D399K, D399R, D399H, S400K, S400R, S400H, Q347K, Q347R, Q347H, V348K, V348R, V348H, Y349K, Y349R, Y349H, T350K, T350R, T350H, F405R, F405K, F405H, Y407R, Y407K and Y407H.

It is an object of this invention to provide a multispecific heterodimeric antibody molecule comprising a first immunoglobulin heavy chain and a second immunoglobulin heavy chain, wherein CH3 domain of the first heavy chain comprises at least two, preferably two to six and most preferably three to four, amino acid mutations, and CH3 domain of the second heavy chain comprises at least two, preferably two to six and most preferably three to four, amino acid mutations, wherein the at least two, preferably two to six and most preferably three to four, mutations in the first heavy chain CH3 domain are mutated to two, preferably two to six and most preferably three to four, positively charged amino acids, and the at least two, preferably two to six and most preferably three to four, mutations in the CH3 domain of the second heavy chain are mutated to two, preferably two to six and most preferably three to four, negatively charged amino acids, wherein the substitutions in the CH3 domain of the second heavy chain are selected from the group consisting of Y391D, Y391E, K392D, K392E, T393D, T393E, T394D, T394E, P395D, P395E, P396D, P396E, V397D, V397E, V397C, L398D, L398E, D399E, S400D, S400E, S354D, S354E, R355E, R355D, F405E, F405D, Y407E, Y407D, K409D and K409E.

It is yet another object of the invention to provide a multispecific antibody molecule comprising a first heavy chain and a second heavy chain, wherein CH3 domain of the first heavy chain comprises at least two, preferably two to six and most preferably three to four, amino acid mutations, and CH3 domain of the second heavy chain comprises at least two, preferably two to six and most preferably three to four, amino acid mutations, wherein the at least two, preferably two to six and most preferably three to four, mutations in the first heavy chain CH3 domain introduce at least two, preferably two to six and most preferably three to four, positive charges to the CH3 domain of the first heavy chain, and the at least two, preferably two to six and most preferably three to four, mutations in the CH3 domain of the second heavy chain introduce at least two, preferably two to six and most preferably three to four, negative charges to the second CH3 domain, and wherein the CH3 domain of the first heavy chain comprises an amino acid sequence according to SEQ ID NO: 5 (OA) and the CH3 domain of the second heavy chain comprises an amino acid sequence according to SEQ ID NO:7 (OB) or according to SEQ ID NO: 11 (OD), or the CH3 domain of the first heavy chain comprises an amino acid sequence is SEQ ID NO: 9 (OC) and the CH3 domain of the second heavy chain comprises an amino acid sequence according to SEQ ID NO:7 (OB).

A further object of the invention is to provide nucleic acid vectors comprising nucleotide sequences that encode the first heavy chain and the second heavy chain of the molecule of any one the previous claims, wherein the coding sequences can be on the same vector or separate vectors, and wherein the ratio of nucleic acid encoding the first chain and the second chain may vary.

A further object of this invention is to provide an isolated polypeptide chain harboring a CH3 domain of an multispecific antibody, said polypeptide chain comprising an amino acid sequence according to SEQ ID selected from the group consisting of SEQ ID NO:1, 3, 5, 7, 9, 11, 13, 15, 16, 17, 19, 21, 23, 25, 27, 29, 31, 33 and 35.

An even further object of this invention is to provide a method to make a multispecific antibody, wherein the method comprises the steps of: a) Providing a first polypeptide including a first CH3 domain, a first CH2 domain and a first antigen binding domain; b) Providing a second polypeptide including a second CH3 domain, a second CH2 domain, and a second antigen binding domain; c) Substituting at least two, preferably two to six and most preferably three to four, amino acids in the CH3 domain of the first polypeptide, wherein the substitutions increase the positive charge of the chain; d) Substituting at least two, preferably two to six and most preferably three to four, amino acids in the CH3 domain of the second polypeptide, wherein the substitutions increase the negative charge of the chain; e) Co-expressing the polypeptide chains of step a) and b) in an appropriate cell line; f) Isolating heterodimers containing the first and the second polypeptide from the dimers expressed by the cell line; and optionally g) Modifying the isolated heterodimers by fusing further units to the polypeptides.

DETAILED DESCRIPTION OF THE INVENTION

Definitions

Figure 1B:
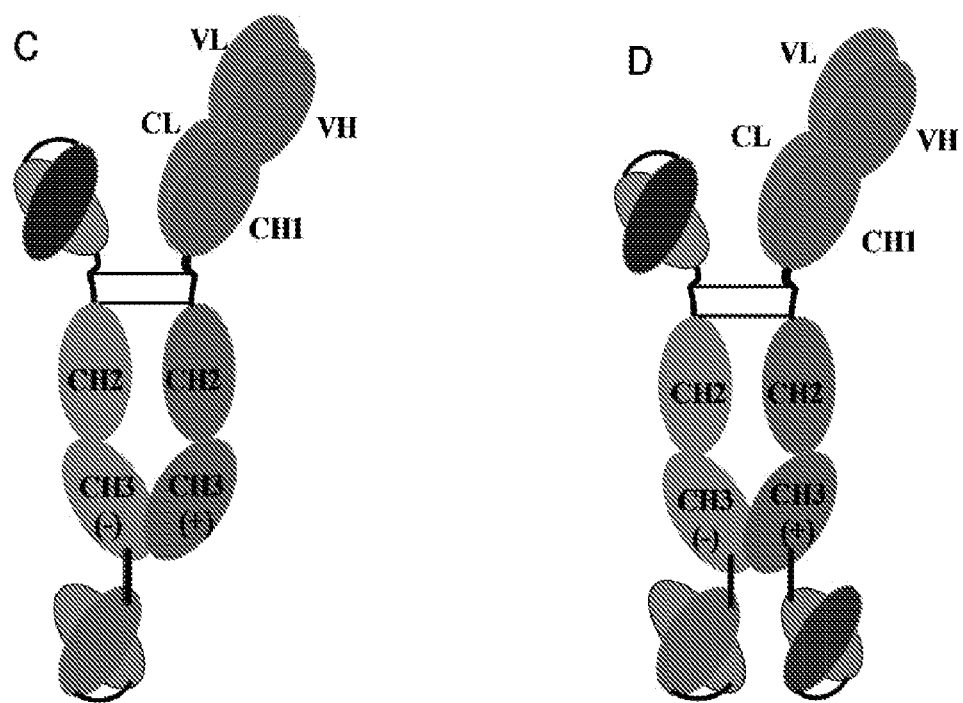
FIG. 1 shows a schematic illustration of examples of bispecific or multi-specific antibody structure from present invention. The present invention provides a molecule that may be a bispecific, tri-specific or quadro-specific antibody. Panel A and B (FIG. 1A) are two common "Y" shaped bispecific antibody structures. Panel C and D (FIG. 1B) illustrates tri-specific and quadro-specific antibody formats derived from panel A. Panel E and F (FIG. 1C) are tri-specific and quadro-specific antibody formats derived from panel B.

By "amino acid" as used herein it is meant one of the 20 naturally occurring amino acids or any non-natural analogues that may be present at a specific, defined position.

By "amino acid mutation" as used herein it is meant an amino acid substitution, insertion, and/or deletion in a polypeptide sequence. The preferred amino acid modification herein is a substitution.

By "amino acid substitution" or "substitution" as used herein it is meant replacement of an amino acid at a particular position in a parent polypeptide sequence with another amino acid. For example, the substitution P395D refers to a variant polypeptide in which amino acid Proline at position 395 of the polypeptide has been replaced by amino acid Aspartic acid By "antibody" as used herein it is meant to include full length antibodies as well as antibody fragments. Antibody may refer to a natural antibody from any organism, an engineered antibody, or an antibody generated by recombinant technologies for experimental, therapeutic, or other purposes. The term "antibody" comprises monoclonal and polyclonal antibodies. Antibodies can be antagonists, agonists, neutralizing, inhibitory, or stimulatory.

By "antibody fragment" as used herein it is meant proteins such as Fab, Fv, scFv, or other antigen-binding subsequences of antibodies, either produced by the modification of whole antibodies or those synthesized de novo using recombinant DNA technologies.

By "bispecific antibody" or "BsAb" as used herein it is meant an artificial protein that is composed of fragments of two different antibodies and consequently binds to two different types of antigens.

By "multispecific antibody" as used herein it is meant bispecific, tri-specific or quadro-specific antibodies. Multispecific antibodies are composed of fragments of two or more different antibodies and consequently bind to two, three or four different proteins.

By "minibody" as used herein it is meant an artificial antibody fragment consisting of an antibody fragment VL-VH-CH3.

By "nanobody" as used herein it is meant Camelid antibody fragment consisting of a single monomeric variable antibody region.

By "probody" as used herein it is an artificial antibody molecule where antigen binding sides are masked until activated.

By "diabody" as used herein it is meant an artificial antibody fragments having dimerized single chain variable fragments.

By "Fab" or "Fab region" as used herein it is meant the polypeptides that comprise the VL, VH, CL, and CH1 immunoglobulin domains or regions.

By "Fc" or "Fc region" or "Fc fragment" as used herein it is meant the polypeptides comprising the last two constant region immunoglobulin domains (CH2 and CH3) of IgA, IgD, and IgG, and the last three constant region immunoglobulin domains of IgE and IgM, and part of the flexible hinge N-terminal to these domains. Although the boundaries of the Fc region may vary, the human IgG heavy chain Fc region is usually defined to comprise residues starting at A231 to its carboxyl-terminus, wherein the numbering is according to the EU numbering scheme.

By "hinge" or "hinge region" as used herein it is meant the flexible polypeptide comprising the amino acids between the first and second constant domains (CH1 and CH2) of an antibody. The hinge is defined structurally for the purposes of the present invention, and "hinge region" as used herein for IgG comprises residues 216-230, wherein numbering is according to the EU numbering scheme.

By "IgG" as used herein it is meant a protein belonging to the class of antibodies that are substantially encoded by a recognized immunoglobulin gamma gene. In humans this class comprises IgG1, IgG2, IgG3, and IgG4.

By "position" as used herein it is meant a location in the sequence of a protein. Positions may be numbered sequentially, or according to an established format, for example the Kabat or EU numbering schemes. For example, position 297 is a position in the human antibody IgG1.

By "protein" as used herein it is meant at least two covalently attached amino acids, which includes proteins, polypeptides, oligopeptides and peptides.

By "wild type or WY" as used herein it is meant an amino acid sequence or a nucleotide sequence that is found in nature, including allelic variations. A WT protein has an amino acid sequence or a nucleotide sequence that has not been intentionally modified.

This disclosure provides novel multi-specific antibody platform to enhance heterodimerization of two differently modified mammalian, preferably human IgG Fc regions (i.e. IgG1, 2, 3, 4 or IgA, IgD, IgE, IgM) the modifications can also include other mammalian antibodies, e.g. mouse mIgG1, mIgG2A, mIgG2B and mIgG3.

Virtually any antigen may be targeted by the antibodies of the present invention. The antibody variants of the present invention may find use in a wide range of antibody products. In one embodiment the antibody variant of the present invention is a therapeutic, a diagnostic, or a research reagent, preferably a therapeutic. The antibody variants may find use in an antibody composition that is monoclonal or polyclonal. In one aspect, the antibody variants of the present invention are used to kill target cells that bear the target antigen, for example cancer cells. In another aspect, the antibody variants of the present invention are used to block, antagonize, or agonize the target antigen, for example for antagonizing a cytokine or cytokine receptor. In one aspect, the antibody variants of the present invention are used to block, antagonize, or agonize the target antigen and kill the target cells that bear the target antigen. The antibody variants of the present invention may be used for various therapeutic purposes. Variety of other therapeutic agents may find use for administration with the antibody variants of the present invention. In one aspect, the antibody may be administered with an anti-angiogenic agent.

Pharmaceutical compositions are contemplated wherein an antibody variant of the present invention and one or more therapeutically active agents are formulated. Formulations of the antibody variants of the present invention are prepared for storage by mixing said antibody having the desired degree of purity with optional pharmaceutically acceptable carriers, excipients or stabilizers (Remington's Pharmaceutical Sciences 16$^{th}$ edition, Osol, A. Ed., 1980), in the form of lyophilized formulations or aqueous solutions. The formulations to be used for in vivo administration are preferably sterile. This is readily accomplished by filtration through sterile filtration membranes or other methods. The antibodies and other therapeutically active agents disclosed herein may also be formulated as immune-liposomes, and/or entrapped in microcapsules.

The concentration of the therapeutically active antibody variant in the formulation may vary from about 0.1 to 100 wt %. In one aspect, the concentration of the antibody is in the range of 0.003 to 1.0 molar. In order to treat a patient, a therapeutically effective dose of the antibody variant of the present invention may be administered. By "therapeutically effective dose" herein it is meant a dose that produces the effects for which it is administered. The exact dose will depend on the purpose of the treatment, and will be ascertainable by one skilled in the art using known techniques. Dosages may range from 0.01 to 100 mg/kg of body weight or greater, for example 0.1, 1, 10, or 50 mg/kg of body weight, with 1 to 10 mg/kg being preferred. As is known in the art, adjustments for antibody degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

Administration of the pharmaceutical composition comprising an antibody variant of the present invention, preferably in the form of a sterile aqueous solution, may be done in a variety of ways, including, but not limited to, orally, subcutaneously, intravenously, intranasally, intraotically, transdermally, topically (e.g., gels, salves, lotions, creams, etc.), intraperitoneally, intramuscularly, intrapulmonary, parenterally, rectally, or intraocularly.

The wild type antibody Fc consists of two identical hinge-CH2-CH3 polypeptide fragments. The binding interaction between two CH3 domains leads to dimerization of two polypeptide fragments. The basic idea in this invention is to increase positive charge distribution on the first CH3 domain and negative charge distribution on the second CH3 domain, thus enhancing CH3 domain heterodimerization and increase the purity of the antibody yield. In order to achieve these goals, the binding interfaces between two CH3 domains in several antibody Fc crystallography structures were studied. Immunoglobulin heavy chain dimer structure was analyzed using protein 3D structure analysis software Cn3D4.3.1. Following IgG X-ray crystallography structures from PDB database were closely examined: 1L6X, 1HZH, 1OQX, 1H3X and 4HAG. Special interests were focused on hinge region, CH3 domain edge interface from N390 to S400, and Q347-E357, and CH3 middle interface from D401 to L410 due to their location at closest proximity between two identical heavy chains. The possible interacting amino acid pairs between two identical heavy chains were identifies as follows:

Hinge Region:
H224-H224
T225-T225
C226-C226
P227-P227
P228-P228
C229-C229
CH3 Edge Interface:
Y391-S400
K392-D399
T393-L398
T394-V397
P395-P396
P396-P395
V397-T394
L398-T393
D399-K392
S400-Y391
5354-T350
R355-Y349
E356-V348
E357-Q347
CH3 Middle Interface:
F405-K409
Y407-Y407
K409-F405

To provide stronger ionic interaction forces and enhance heterodimer formation between two differently modified heavy chains, amino acid mutation scanning approach was employed to walk through above described interfaces between two CH3 domains to identify best mutation combinations. Various numbers of amino acid mutation pairs were tested. In addition to the CH3 mutations, possible hinge region mutations were also evaluated by mutation scanning.

Briefly, at least 2, preferably 2 to 6 and most preferably 3 to 4 positively charged amino acids (arginine, histidine or lysine, etc.), either consecutively or separately, were introduced into possible interacting amino acid positions on the first heavy chain. At the same time, at least 2, preferably 2 to 6 and most preferably 3 to 4 negatively charged amino acids (aspartic acid or glutamic acid, etc.), either consecutively or separately, were introduced into possible interacting amino acid positions on the second heavy chain in the regions described above. The DNA constructs for mutagenesis were purchased from InvivoGen (San Diego, Calif.). pFUSE-CHIg-hG1 is for expression of CH1-hinge-CH2-CH3 fragment driven by human elongation factor 1 promoter, an IL-2 secretion signal sequence was added in front of N terminus of CH1 to make the expression product secreted from host cells by routine molecular cloning. pFUSE-hIgG1-Fc2 is for expression of hinge-CH2-CH3 fragment driven by the same promoter.

Amino acid mutagenesis was carried out by using Quikchange Mutagenesis Kit purchased from Agilent Technologies. All DNA mutagenesis oligo primers were ordered from Life Technologies. A series of amino acid substitution groups were generated as described below:

Hinge Region:
1. Hinge region in chain A (H1):
H224E, T225P, P227G, P228E
Chain A has amino acid sequence according to SEQ ID NO:1 and is encoded by nucleic acid sequence according to SEQ ID NO:2.
2. Hinge region in chain B (H2):
T225R, P227K, P228S
Chain B has amino acid sequence according to SEQ ID NO:3 and is encoded by nucleic acid sequence according to SEQ ID NO:4.
CH3 Edge Interface:
3. Edge interface in chain A (OA):
P395K, P396K, V397K
Chain OA has amino acid sequence according to SEQ ID NO:5 and is encoded by nucleic acid sequence according to SEQ ID NO:6.
4. Edge interface in chain B (OB):
T394D, P395D, P396D
Chain OB has amino acid sequence according to SEQ ID NO:7 and is encoded by nucleic acid sequence according to SEQ ID NO:8.
5. Edge interface in chain A (OC):
P395K, P396K, V397C
Chain OC has amino acid sequence according to SEQ ID NO:9 and is encoded by nucleic acid sequence according to SEQ ID NO:10.
6. Edge interface in chain B (OD):
T394C, P395D, P396D
Chain OD has amino acid sequence according to SEQ ID NO:11 and is encoded by nucleic acid sequence according to SEQ ID NO:12.
7. Edge interface in chain A (OG):
P395R, P396R, V397R
Chain OG has amino acid sequence according to SEQ ID NO:13 and is encoded by nucleic acid sequence according to SEQ ID NO:14.
8. Edge interface in chain B (OH):
T394E, P395E, P396E
Chain OH has amino acid sequence according to SEQ ID NO: 15 and is encoded by nucleic acid sequence according to SEQ ID NO: 16.

9. Edge interface in chain A (OI):
T393K, T394K, P395K

Chain OI has amino acid sequence according to SEQ ID NO: 17 and is encoded by nucleic acid sequence according to SEQ ID NO:18.

10. Edge interface in chain B (OJ):
P396D, V397D, L398D

Chain OJ has amino acid sequence according to SEQ ID NO: 19 and is encoded by nucleic acid sequence according to SEQ ID NO:20.

11. Edge interface in chain A (OM):
T394K, P395K, P396K

Chain OM has amino acid sequence according to SEQ ID NO: 21 and is encoded by nucleic acid sequence according to SEQ ID NO:22.

12. Edge interface in chain B (ON):
P395D, P396D, V397D

Chain ON has amino acid sequence according to SEQ ID NO:23 and is encoded by nucleic acid sequence according to SEQ ID NO:24.

13. Edge interface in chain A (OP):
P396K, V397K, L398K

Chain OP has amino acid sequence according to SEQ ID NO:25 and is encoded by nucleic acid sequence according to SEQ ID NO:26.

14. Edge interface in chain B (OQ):
T393D, T394D, P395D

Chain OQ has amino acid sequence according to SEQ ID NO:27 and is encoded by nucleic acid sequence according to SEQ ID NO:28.

15. Edge interface in chain A (OS):
S354D, R355D

Chain OS has amino acid sequence according to SEQ ID NO:33 and is encoded by nucleic acid sequence according to SEQ ID NO:34.

16. Edge interface in chain B (OT)
V348K, Y349K, T350K

Chain OT has amino acid sequence according to SEQ ID NO: 35 and i encoded by nucleic acid sequence according to SEQ ID NO:36.

CH3 Middle Interface:

17. Middle interface in chain A (OE):
F405E, Y407E, K409E

Chain OE has amino acid sequence according to SEQ ID NO:29 and is encoded by nucleic acid sequence according to SEQ ID NO:30.

18. Middle interface in chain B (OF):
F405K, Y407K

Chain OF has amino acid sequence according to SEQ ID NO:31 and is encoded by nucleic acid sequence according to SEQ ID NO:32.

Other possible mutations may be selected from the following list:

19. Edge interface in chain A (OU):
Y391K, K392, T393K

20. Edge interface in chain B (OV):
L398D, D399, S400D

21. Edge interface in chain A (OK):
K392, T393K, T394K

22. Edge interface in chain B (OL):
D399, L398D, V397D

23. Edge interface in chain A (OW):
V397K, L398K, D399K

24. Edge interface in chain B (OX):
K392, T393D, T394D

25. Edge interface in chain A (OY):
L398K, D399K, S400K

26. Edge interface in chain B (OZ):
Y391D, K392D, T393D

27. Edge interface in chain A (OS):
S354D, R355D

28. Edge interface in chain B (OT)
V348K, Y349K, T350K

29. Edge interface in chain A (RS):
S354D, R355E

30. Edge interface in chain B (RT)
Q347R, Y349R, T350R

In other aspects of this invention, mutation H1 can be combined with mutation OA and OC. Mutation H2 can be combined with mutation OB and OD. Yet in another embodiment, mutation OE can be combined with OA, OB, OC and OD; mutation OF can be combined with mutation OA, OB, OC and OD. Other combinations of the above chains may also be made.

A broad variety of antibodies can be used as source antibodies for constructing present heterodimer molecules, including monoclonal antibodies, chimeric antibodies, human or humanized antibodies, diabodies, Single chain Fv (scFv), heavy chain only antibodies (eg. Nanobody), fibronectin binding domains, multi-specific antibodies and antibody conjugates. The source antibodies can be from any isotypes (eg. IgG, IgE, IgD, IgA, IgM and IgY, etc), and any subclasses (eg. IgG1, IgG2, IgG3, IgG4, IgA1, IgA2, mIgG2a and mIgG2b, etc). The source antibodies can recognize a broad variety of protein or non-protein targets known to the art.

Figure 2:
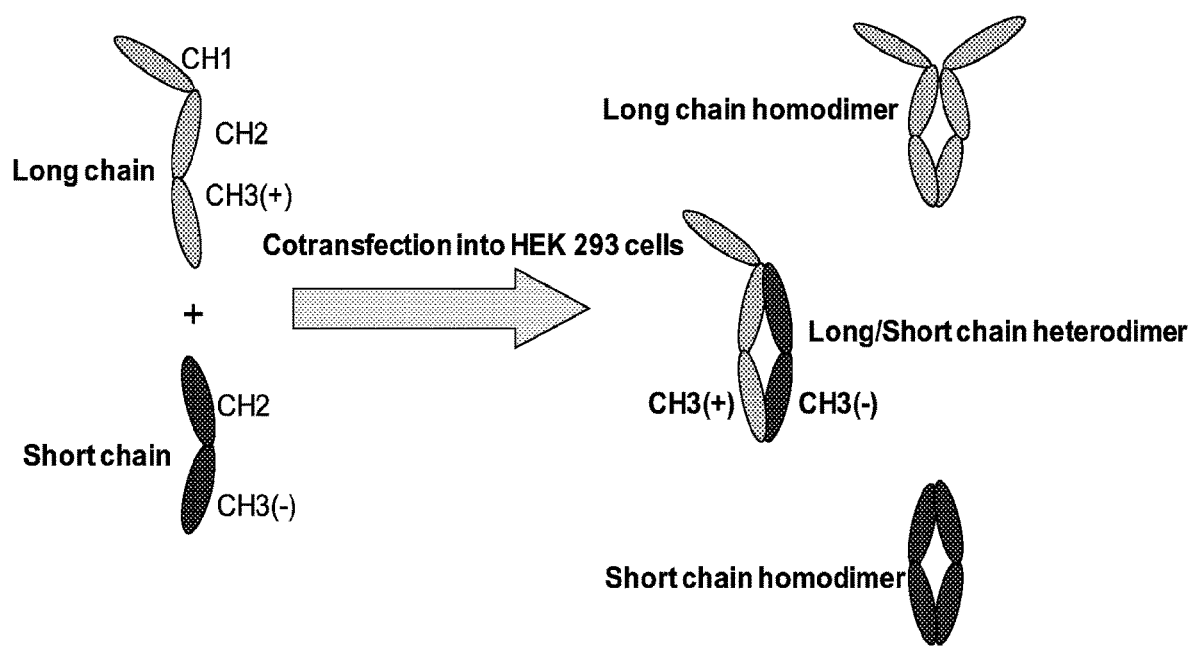
FIG. 2 is a schematic illustration of an experiment procedure for evaluation of heterodimeric formation between two modified CH3 containing polypeptide fragments. A long chain usually contains CH1-hinge-CH2-CH3 with positively charged amino acid substitutions, whereas a short chain usually contains only hinge-CH2-CH3 with negatively charged amino acid substitutions. DNA encoding long chain and short chain were mixed with 1:1 ratio and transfected into HEK293 cells. Three days later, cell culture supernatants were harvested and subjected to magnetic protein A beads pull-down. Proteins bound to magnetic beads were analyzed by SDS-PAGE electrophoresis.

FIG. 2 shows a schematic illustration of an experimental procedure to evaluate the heterodimer formation between two modified heavy chains. In FIG. 2, for an example, the first chain is a long chain including CH1, hinge region, CH2 and CH3. The second chain is short chain including only hinge region, CH2 and CH3. The CH3 domain of the first chain was mutated by amino acid substitution so as to increase the positive charge of the CH3 domain. Preferably the first chain included two to six amino acid mutations. However, 3 or 4 amino acid mutations provided the most preferred results. The mutation sites were preferably selected at edge interface from Y391 to 5400 (e.g. Y391, K392, T393, T394, P395, P396, V397, L398, D399 and S400), edge interface from Q347 to E357 (Q347, V348, Y349, T350, S354, R355, E356, E357) and middle interface from D401 to L410 (F405, Y407, and K409). Most preferable substitutions were selected from the group consisting of T393K, T394K, P395K, P396K, V397K, V397C, L398K, V348K, Y349K and T350K. However, other substitutions could also be used as long as the positive charge of the CH3 domain is increased by the substitution combination. In present invention, EU antibody amino acid numbering system was used.

Figure 1C:
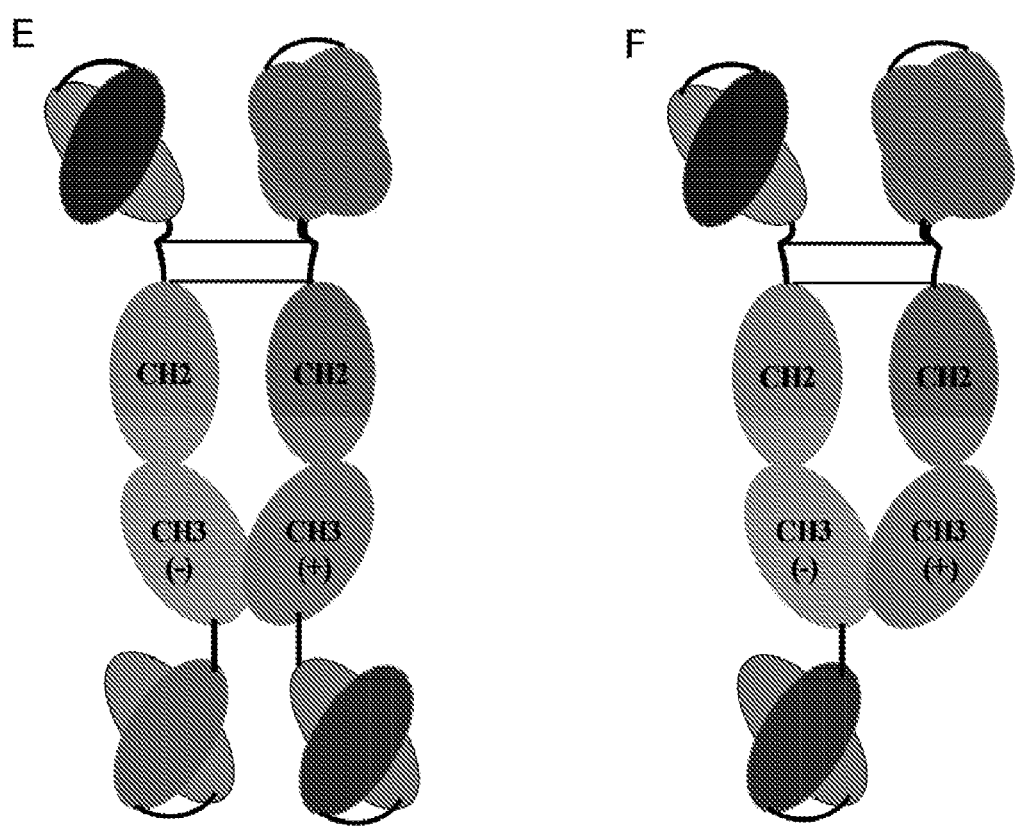

The second chain as shown in FIG. 2 is for an example a short chain including only hinge region, CH2 and CH3. The CH3 of the second chain was mutated by amino acid substitution in the second chain so as to increase the negative charge of the CH3 domain. Preferably the second chain included two to six such amino acid mutations. However, 3 or 4 amino acid mutations provided the most preferred results. The mutation sites were preferably selected at edge interface from Y391 to 5400 (Y391, K392, T393, T394, P395, P396, V397, L398, D399 and S400), edge interface from Q347 to E357 (Q347, V348, Y349, T350, S354, R355, E356, E357) as well as middle interface from D401 to L410 (F405, Y407, and K409). Most preferable substations were selected from the group consisting of T393D, T394D, P395D, P396D, V397D, V397C, L398D, S354D and R355D. However, other substitutions could also be used as long as the negative charge of the CH3 domain is increased by the substitution combination. The complementary pairs of mutated chains were co-transfected into human embryonic kidney HEK 293 cells. Other mammalian cell lines, such as Chinese Hamster Ovary (CHO) cells and mouse NS0 cells could be used as well. As a result of the co-transfection, the mutated long chain and short chain would dimerize in three possible ways as is shown in right hand side of FIG. 2. Part of the dimers would be long chain homodimers, another part of them would be long/short chain heterodimers and the third part of them would be short chain homodimers. The preferred heterodimeric antibody is the long/short chain heterodimer. In FIG. 1 one such bispecific antibody structure is schematically shown. The short heavy chain as shown in FIG. 1 comprises mutated CH3 with increased negative charge, a non-mutated CH2, and a hinge region attached to a single chain variable fragment ScFv against Antigen A. The long heavy chain comprises CH3 domain mutated to include increased positive charge, a non-mutated CH2, a hinge region attached to an antigen binding fragment Fab against antigen B. Panel C and D in FIG. 1 illustrate tri-specific and quadro-specific antibody formats derived from panel A. Panel E and F are tri-specific and quadro-specific antibody formats derived from panel B.

The increased positive charge in the long heavy chain and the increased negative charge in the short heavy chain increases the yield of short/long chain heterodimers (see FIG. 2) due to the stronger electrostatic attraction between negative and positive charges in the CH3 domains of two chains. For this reason, the yield of the preferred heterodimers is higher.

The increased negative charges in the short heavy chain CH3 domain results also into another specific feature of the antibodies according to this invention; namely that only the positively charged long chain Fc is capable of binding to protein A, an antibody purification reagent; the negatively charged short chain Fc does not bind to protein A. This feature can now be used to further purify the heterodimer antibody produced from the co-transfected HEK293 cell culture.

Figure 8:
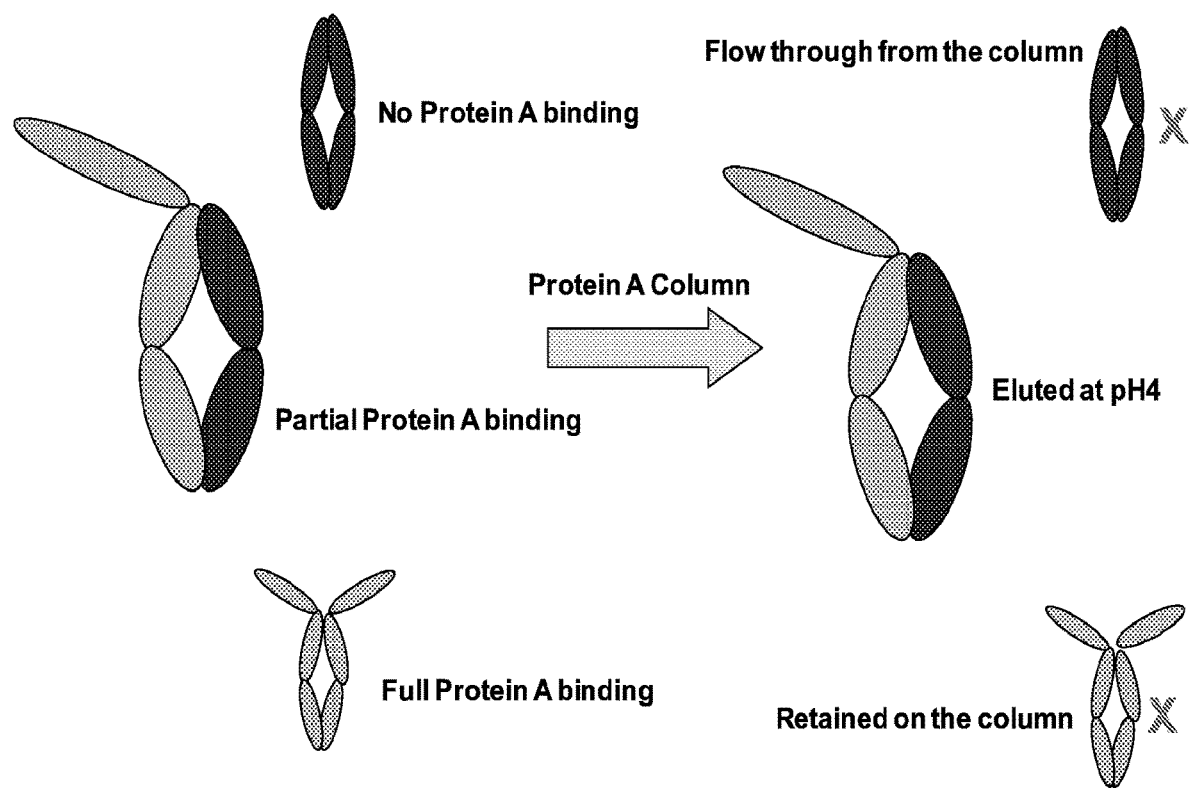
FIG. 8 is a schematic illustration of the single step protein A column purification for the antibodies of this invention. Short chain harbors a mutation that lost protein A binding activity, and its homodimer, if there is any, will flow through the column during the wash step. On the other hand, Long chain harbors a mutation that retained protein A binding, and its homodimer, if there is any, will retain on the column when elution at pH above 3. Only long chain and short chain heterodimer can be eluted out at pH between 4.0 and 5.0.

As is shown in FIG. 2, the antibodies received are of three different types; long chain homodimers, long/short chain heterodimers and short chain homodimers. FIG. 8 shows a schematic illustration of a purification step that is based on the above described specific feature of the short/long chain heterodimer. When the yield of the antibodies received from the co-transfected cell culture is run through a protein A affinity column, the short chain homodimers will flow through the column as they no longer bind to protein A. The homodimers having two long chains will bind strongly to protein A in the column whereas the heterodimers will bind to protein A with lower affinity due to the fact that only long chain Fc provides binding to protein A. By eluting the column with an elution solution having a pH of 4 or above, the heterodimer will be eluted out, but the long chain homodimers will not be eluted out due to their stronger binding to the column. Therefore, the heterodimer is the only species to be eluted at this pH.

Accordingly, this invention provides at least two benefits: first of all, the yield of long chain/short chain heterodimer formation is increased in the co-transfection due to the stronger attraction between negative and positive charges in the CH3 domains; preferably 90-95% of the dimers are heterodimers. Secondly the preferred short chain/long chain heterodimers can be purified in a single step protein A affinity column by using a higher pH elution solution.

In the above description the heavy chains are described as being short chain and long chain because the exemplary bispecific antibodies shown in FIG. 1 have short heavy chain and long heavy chain. However, it is not necessary to have short and long heavy chains. Both of the chains may be attached to ScFv antigen binding fragments or both of the chains may have Fab antigen binding fragments. In the above description the antibody as shown in FIG. 1 is a bispecific antibody having two binding sites to two different proteins, but as well the antibody could be tri or quadro-specific and having three or four different antigen binding sites. Those binding domains with different specificities can be fused to N terminus or C terminus of both dimeric heavy chains as is shown in FIG. 1 panels C-F.

According to another aspect of the invention, additional mutations are created in the hinge regions of the heavy chains. Most preferably the mutations in the hinge regions locate at one or more of the amino acid in positions H224, T225, P229 or P228. At least one hinge region mutation in the first heavy chain is preferably selected from H334E, T225P, P229G and P228G and at least one mutation in the second heavy chain hinge region are selected from T225R, P227S, and P228K.

It is to be understood that the antibody platform described here can be applied to any type of bi- or multispecific antibodies having the Fc-region. Moreover, it is to be understood that the antigen binding fragments may be chosen as desired. The antibodies of this invention may be anti-cancer antigen antibodies, they may be specific for non-cancer proteins that are associated with cancer development or invasiveness, or they may be specific for example to virus-associated proteins. Virtually any antigen may be targeted by the antibodies of the present invention, including but are not limited to proteins, subunits, domains, motifs, and epitopes belonging to the following list of proteins: CD2; CD3, CD3E, CD4, CD11, CD11a, CD14, CD16, CD18, CD19, CD20, CD22, CD23, CD25, CD28, CD29, CD30, CD32, CD33 (p67 protein), CD38, CD40, CD40L, CD52, CD54, CD56, CD80, CD147, GD3, IL-1, IL-1R, IL-2, IL-2R, IL-4, IL-5, IL-6, IL-6R, IL-8, IL-12, IL-15, IL-18, IL-23, interferon alpha, interferon beta, interferon gamma; TNF-alpha, TNFbeta2, TNFα, TNFalphabeta, TNF-R1, TNF-RII, FasL, CD27L, CD30L, 4-1BBL, TRAIL, RANKL, TWEAK, APRIL, BAFF, LIGHT, VEG1, OX40L, TRAIL Receptor-1, A1 Adenosine Receptor, Lymphotoxin Beta Receptor, TACI, BAFF-R, EPO; LFA-3, ICAM-1, ICAM-3, EpCAM, integrin beta1, integrin beta2, integrin alpha4/beta7, integrin alpha2, integrin alpha3, integrin alpha4, integrin alpha5, integrin alpha6, integrin alphav, alphaVbeta3 integrin, FGFR-3, Keratinocyte Growth Factor, VLA-1, VLA-4, L-selectin, anti-Id, E-selectin, HLA, HLA-DR, CTLA-4, T cell receptor, B7-1, B7-2, VNR integrin, TGFbeta1, TGFbeta2, eotaxin1, BlyS (B-lymphocyte Stimulator), complement C5, IgE, factor VII, CD64, CBL, NCA 90, EGFR (ErbB-1), Her2/neu (ErbB-2), Her3 (ErbB-3), Her4 (ErbB4), Tissue Factor, VEGF, VEGFR, endothelin receptor, VLA-4, Hapten NP-cap or NIP-cap, T cell receptor alpha/beta, E-selectin, digoxin, placental alkaline phosphatase (PLAP) and testicular PLAP-like alkaline phosphatase, transferrin receptor, Carcinoembryonic antigen (CEA), CEACAM5, HMFG PEM, mucin MUC1, MUC18, Heparanase I, human cardiac myosin, tumor-associated glycoprotein-72 (TAG-72), tumor-associated antigen CA 125, Prostate specific membrane antigen (PSMA), High molecular weight melanoma-associated antigen (HMW-MAA), carcinoma-associated antigen, Gcoprotein Iib/IIIa (GPIIb/IIIa), tumor-associated antigen expressing Lewis Y related carbohydrate, human cytomegalovirus (HCMV) gH envelope glycoprotein, HIV gp120, HCMV, respiratory syncital virus RSV F, RSVF Fgp, VNR integrin, IL-8, cytokeratin tumor-associated antigen, Hep B gp120, CMV, gpIIbIIIa, HIV IIIB gp120 V3 loop, respiratory syncytial virus (RSV) Fgp, Herpes simplex virus (HSV) gD glycoprotein, HSV gB glycoprotein, HCMV gB envelope glycoprotein, and *Clostridium perfringens* toxin.

The antibodies that may be selected from include, but not limited to antibodies against following antigens: PSMA, CD133, CD138, CD20, CD19, OX40, GITR, PD-1, PD-L1 or PD-L2, CTLA-4, KIR, LAG-3, CD3, TCRα, TCRβ, TCRγ, TCRδ, CD40, CD40L, VEGF, EGF, VEGFR, EGFR, Her1, Her2, Her3, EpCAM, Mesothelin, Glypicans, CD28, Erb1, Erb2, B7-H3, ICOS, BMP1, BMP2, BMP3B, BMP4, CSF1, GM-CSF, FGF1, FGF2, FGF3, FGF4, PDGFR, TIGIT, CS1, TWEAK, CCL1, CCL2, CCL3, CCL13, CXCL1, CXCL2, CXCL3, IP-10, Fucosyl-GM1, IGF1, IGF2, IGF1R, IGF2R, CD64, CD32a, CD32b, CD16, Integrins, RANK ligand, CEA, DLL-4, GM-CSFR, ADAMS, Myostatin, PCSK9, CXCR4, IL-1 alpha, IL-1 beta, IL-12, IL-18, TNF alpha, IL-23, IL-13, MIF, IL-17, IL-17R, IL-15, IL-9, IL-5, IL-5R, IL-6, IL-25, PEG2, etc.

Alternatively, the antibodies of this invention may be specific for virus-associated targets, such as HIV proteins, HPV proteins, CMV-proteins, influenza virus proteins or prion proteins.

In certain aspects, the molecules of this invention can be used for diagnostic and therapeutic applications. More specifically, the molecules from the present invention can be used to generate bi-specific or multi-specific antibodies that can bind to two or more than two target antigens selected from, but not limited to following target list: IL-1 alpha, IL-1 beta, IL-12, IL-18, TNF alpha, IL-23, IL-13, MIF, IL-17, IL-17R, IL-15; VEGF, VEGFR, EGFR; IL-9, IL-5, IL-5R, IL-6, IL-25, IL-13, ADAMS, PEG2, Her1, Her2 and Her3. A skilled artisan would be able to recognize other possible targets.

The invention is now described by means of non-limiting examples.

Example 1: Identification of Amino Acid Residues Responsible for Ionic Interactions in Immunoglobulin Fc Region Immunoglobulin heavy chain dimer structure was analyzed using Protein 3D structure analysis software Cn3D4.3.1. Following IgG X-ray crystallography structures from PDB database were closely examined: 1L6X, 1HZH, 1OQX, 1H3X and 4HAG. Special interest was focused on hinge region, CH3 domain edge interface from N390 to 5400 and CH3 middle interface from D401 to L410 due to their tight closeness between two identical heavy chains. The possible interaction amino acid residue pairs between two identical heavy chains are listed below:
Hinge Region:
H224-H224
T225-T225
C226-C226
P227-P227
P228-P228
C229-C229
CH3 Edge Interface:
Y391-5400
K392-D399
T393-L398
T394-V397
P395-P396
P396-P395
V397-T394
L398-T393
D399-K392
S400-Y391
5354-T350
R355-Y349
E356-V348
E357-Q347
CH3 Middle Interface:
F405-K409
Y407-Y407
K409-F405
EU antibody amino acid numbering system is used in this invention for amino acid numbering.

Example 2: Modification of the Amino Acids in the Heavy Chains to Promote Heterodimer Formation To provide appropriate ionic interaction forces and enhance heterodimer formation between two differently modified heavy chains, at least 2, preferably 2 to 6 and most preferably 3 to 4 positively charged amino acids (arginine or lysine, etc.), either consecutively or separately, were introduced into possible interaction amino acid locations on the first heavy chain. At the same time, at least 2, preferably 2 to 6 and most preferably 3 to 4 negatively charged amino acids (aspartic acid or glutamic acid, etc.), either consecutively or separately, were introduced into possible interaction amino acid locations on the second heavy chain in the regions described above. The vector constructs for mutagenesis were purchased from InvivoGen (San Diego, Calif.): pFUSE-CHIg-hG1 is for expression of CH1-hinge-CH2-CH3 fragment driven by human elongation factor 1 promoter, an IL-2 secretion signal sequence was added in front of N terminus of CH1 to make the expression product secreted from host cells by routine molecular cloning. pFUSE-hIgG1-Fc2 is for expression of hinge-CH2-CH3 fragment driven by the same promoter.

Amino acid mutagenesis was carried out by using Quickchange Mutagenesis Kit purchased from Agilent Technologies. All DNA mutagenesis oligo primers were ordered from Life Technologies. Amino acid mutation scanning approach was utilized to walk through heavy chain hinge region, CH3 edge interface and middle interface to identify best mutant combinations of generating high purity heterodimers. A series of amino acid substitution groups were listed below:
Hinge Region:
  1. Hinge region in chain A (H1, negative charged):
  H224E, T225P, P227G, P228E
  2. Hinge region in chain B (H2, positive charged):
  T225R, P227K, P228S
CH3 Edge Interface:
  3. Edge interface in chain A (OA, positive charged):
  P395K, P396K, V397K
  4. Edge interface in chain B (OB, negative charged):
  T394D, P395D, P396D
  5. Edge interface in chain A (OC, positive charged and disulfide bond formation):
  P395K, P396K, V397C
  6. Edge interface in chain B (OD, negative charged and disulfide bond formation):
  T394C, P395D, P396D
  7. Edge interface in chain A (OG, positive charged):
  P395R, P396R, V397R 8. Edge interface in chain B (OH, negative charged): T394E, P395E, P396E
9. Edge interface in chain A (OI, positive charged): T393K, T394K, P395K
10. Edge interface in chain B (OJ, negative charged): P396D, V397D, L398D
11. Edge interface in chain A (OM, positive charged): T394K, P395K, P396K
12. Edge interface in chain B (ON, negative charged): P395D, P396D, V397D
13. Edge interface in chain A (OP, positive charged): P396K, V397K, L398K
14. Edge interface in chain B (OQ, negative charged): T393D, T394D, P395D
15. Edge interface in chain A (OS, negative charged): S354D, R355D
16. Edge interface in chain B (OT, positive charged) V348K, Y349K, T350K CH3 Middle Interface:
17. Middle interface in chain A (OE, negative charged): F405E, Y407E, K409E
18. Middle interface in chain B (OF, positive charged): F405K, Y407K Mutation H1 may also be combined with mutation OA or OC. Mutation H2 may be combined with mutation OB or OD. Those combined mutations not only produce sufficient amount of proteins that bind to protein A, but also favor heterodimer formation. However, significant amount of single chain monomer was presented in the final products, which may require at least one more purification step to remove.

Mutation OE may be combined with OA, OB, OC and OD; mutation OF may be combined with mutation OA, OB, OC and OD. However, those combined mutations couldn't produce sufficient amount proteins that bind to protein A.

Example 3: Co-Transfection of HEK 293 Cells and Protein Product Analysis

Experiment procedure utilized to evaluate the heterodimer formation effect was illustrated in FIG. 2. Mutated polypeptide chain A incorporated with positively charged amino acids (usually long chain in the figure) and mutated polypeptide chain B incorporated with negatively charged amino acids (usually short chain in the figure) were transfected into HEK293 cells either alone or together with each other using 293fectin transfection reagent from Life Technologies. Various positive charged and negative charged polypeptide chain combinations were co-expressed in HEK 293 cells. The preferred ratio between positively charged polypeptide chain and negatively charged polypeptide chain is 1:1 in present invention, but other ratios can be used as well. Three days after transfection, cell culture supernatants were harvested by centrifugation and subjected to protein A magnetic beads (Pierce) pull down. Protein products bound on magnetic beads were characterized based on their mobility on SDS-PAGE gel electrophoresis. Collected protein A magnetic beads with bound proteins were re-suspended in 30 μL PBS buffer, mixed with 30 μL of SDS-PAGE loading buffer and boiled for 5 min. Half volume of boiled samples was loaded onto 10% SDS-PAGE to separate long chain homodimer, long chain and short chain heterodimer and short chain homodimer. Some of representative heterodimer formation results are shown in FIGS. 3, 4, 5, 6 and 7.

Figure 3:
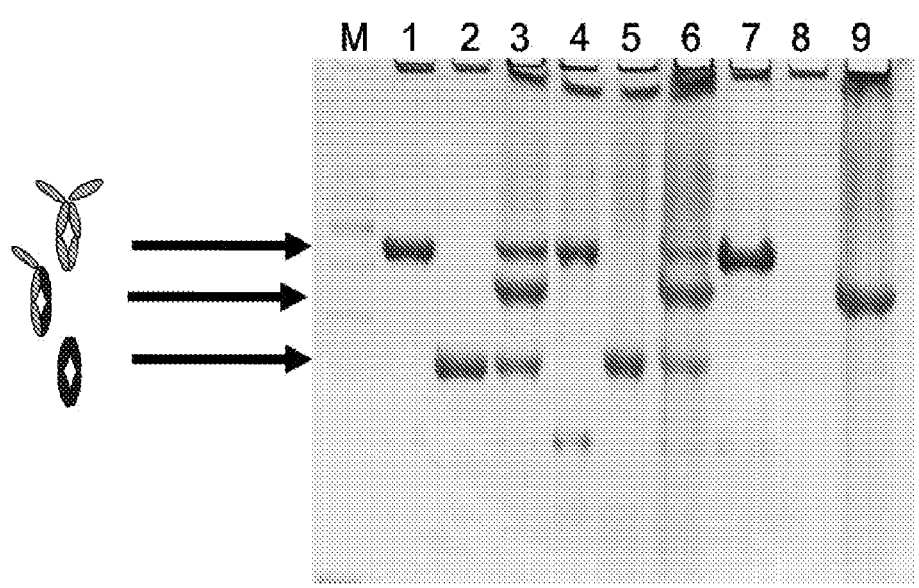
FIG. 3 shows a SDS-PAGE gel loaded with various samples: M: Marker; Lane 1: WT long chain; Lane 2: WT short chain; Lane 3: Co-transfection of WT long chain and short chain. In addition to heterodimer band in the middle, there are significant amounts of long chain homodimer (top) and short homodimer (bottom); Lane 4: Mutant OE chain; Lane 5: Mutant OF chain; Lane 6: Co-transfection of OE and OF chains; Lane 7: Mutant OA chain; Lane 8: Mutant OB chain. Note that OB's binding activity to protein A is lost; Lane 9: Co-transfection of OA and OB chains. Note that the intensity of heterodimer band is comparable to that of WT heterodimer band in lane 4, whereas both long chain and short chain homodimer bands are invisible.

FIG. 3 shows SDS-PAGE gels loaded with the following samples: M: Marker; Lane 1: WT long chain; Lane 2: WT short chain; Lane 3: Co-transfection of WT long chain and WT short chain. Note that in addition to heterodimer band in the middle, there are significant amount of long chain homodimer (top) and short chain homodimer (bottom); Lane 4: OE mutation chain; lane 5: OF mutation chain; lane 6: Co-transfection of OE and OF chains; lane 7: OA mutation chain; lane 8: OB mutation chain; lane 9: Co-transfection of OA and OB chains. On the left hand side of the drawing the structure corresponding to each protein band is shown. Long chain/short chain heterodimer is clearly present in lanes 3, 6 and 9. Lane 3 also shows significant amount of long chain homodimer and short chain homodimer. Similarly, lane 6 shows both homodimers in addition to heterodimer band, however in smaller amount than lane 3. Lane 9 is substantially clean from both homodimers and shows mainly heterodimer. Based on this result, it seems that co-expression of OA chain and OB chain gives high yield of short/long chain heterodimeric antibody. The mutations in OA chain are as follows: P395K, P396K and V397K. The mutations in OB chain are T394D, P395D and P396D. The second best combination seems to be co-expression of OE and OF. The mutations in OE are as follows: F405E, Y407E and K409E. The mutation in OF are as follows: F405K, Y407K.

One important aspect of present example is that the product yield of mutation OE/OF and mutation OA/OB heterodimer is comparable to that of wild type heterodimer. It suggested that those mutations did not compromise the protein expression level in a common mammalian cell expression system, which is critical for large scale manufacture of multi-specific antibodies.

Another important aspect of present example is that mutation OB has lost almost all its binding activity to protein A as indicated in lane 8. However, it is still able to form heterodimer with OA mutation. It is not uncommon in heterodimeric heavy chains that one of the mutated Fc chains may lose its binding activity to protein A, but can form a protein A bound heterodimer as long as the second chain can still bind to protein A (J. H. Davis et al, Protein Engineering, Design & Selection, 2010, 23:4, 195-202). This special feature becomes a technical advantage in heterodimeric antibody purification, as discussed in FIG. 8.

Figure 4:
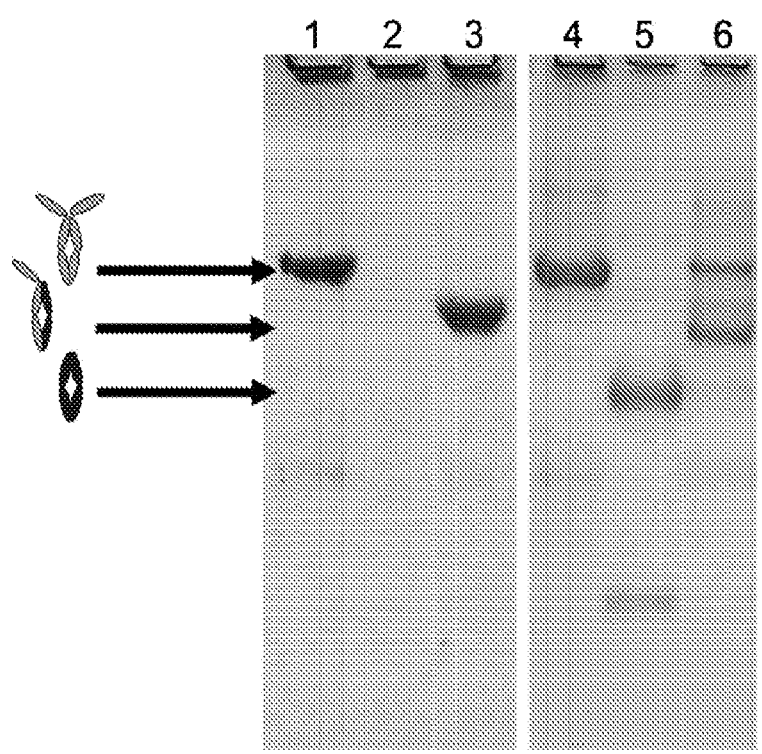
FIG. 4 Shows a SDS-PAGE gel loaded with various samples: Lane 1: Mutation OA chain; Lane 2: Mutation OB chain; Lane 3: Co-transfection of OA and OB chains: Lane 4: Mutation OC chain; Lane 5: Mutation OD chain; Lane 6: Co-transfection of OC and OD chains. Note that there are two heterodimer bands in lane 6.

FIG. 4 shows SDS-PAGE gels loaded with the following samples: Lane 1: OA chain; Lane 2: OB chain; Lane 3: Cotransfection of OA chain and OB chain; Lane 4: OC chain, lane 5: OD chain; lane 6: Cotransfection of OC chain and OD chain. On the left hand side of the drawing the structure corresponding to each protein band is shown. The data from lane 1 to 3 shows the similar results as lane 7 to 9 in FIG. 3, indicating those results are reproducible. The mutations in OC chain are as follows: P395K, P396K and V397C. The mutations in OD chain are T394C, P395D and P396D. Instead of having three positively charged amino acids in long chain pair with three negatively charged amino acids in short chain, two cysteines were introduced on both chains to allow an inter-chain disulfide bond formation between V397C and T394C, which presumably will enhance heterodimer formation. However, co-expression of OC chain and OD chain in HEK293 cells gives rise to two heterodimer bands, as shown in lane 6. It is suggested that the disulfide bond formation is incomplete, which increases the heterogeneity of the product. According to some publications, the heterodimer with an extra disulfide bond in lower middle band usually migrates faster than normal heterodimer in upper middle band (A. M. Merchant et al, Nature Biotechnology, 1998:16). In addition, long chain homodimers are clearly present in this combination.

Figure 5:
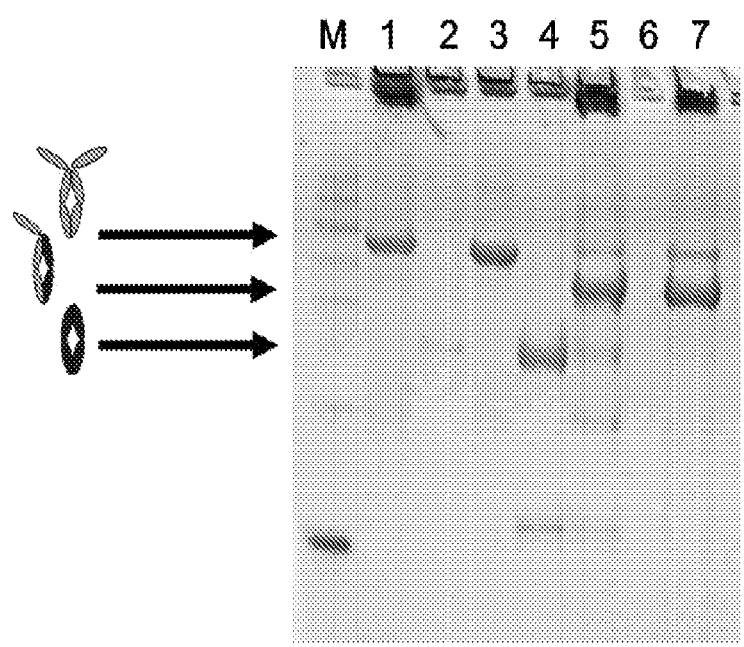
FIG. 5 shows a SDS-PAGE gel loaded with various samples. Lane M: Marker; Lane 1: Mutation OA chain; Lane 2: Mutation OB chain; Lane 3: Mutation OC chain; Lane 4: Mutation OD chain; lane 5: Co-transfection of OA and OD chains; Lane 6: Empty; Lane 7: Cotransfection of OC and OB chains.

FIG. 5 shows SDS-PAGE gels loaded with the following proteins: Lane M: Marker; Lane 1: OA chain; Lane 2: OB chain; Lane 3: OC chain; Lane 4: OD chain; Lane 5: Co-transfection of OA chain and OD chain; Lane 6: empty; Lane 7: Co-transfection of OC chain and OB chain. On the left hand side of the drawing the structure corresponding to each protein band is shown. Lane 5 and 7 show major short/long chain heterodimer antibodies. Both of these lanes also show traces of the homodimers. Based on this result it seems that co-transfection of OA chain and OD chain as well as co-transfection of OC chain and OB chain give relatively higher yield of heterodimeric chains. The mutations in OA chain are as follows: P395K, P396K, and V397K. The mutations in OD chain are T394C, P395D and P396D. The mutations in OC chain are P395K, P396K, C397C and the mutations in OB chain are: T394D, P395D and P396D.

Figure 6:
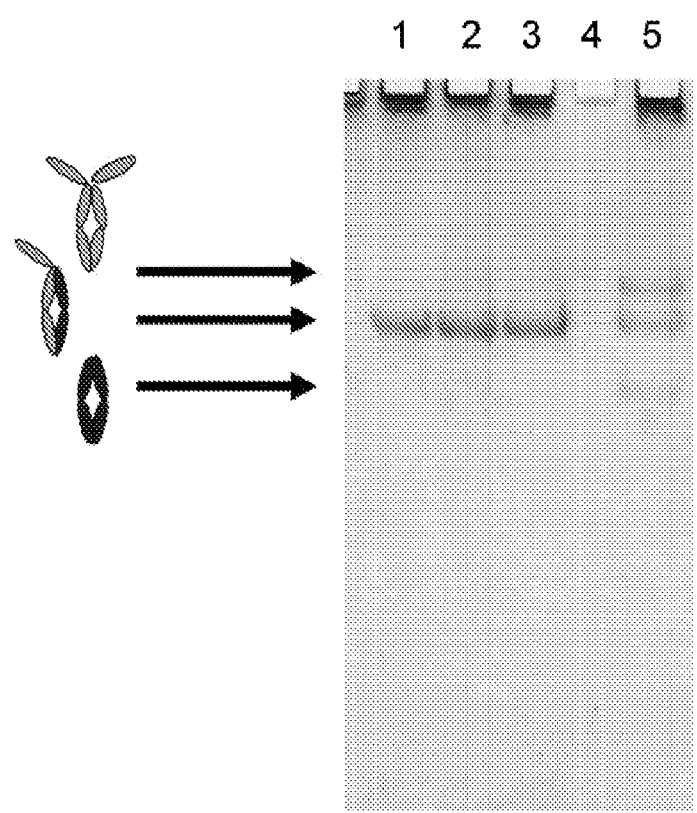
FIG. 6 shows a SDS-PAGE gel loaded with various samples. Lane 1 through 3: Three independent co-transfections of OA and OB chains; Lane 4: Empty; Lane 5: Co-transfection of wild type long chain and short chain as a control.

FIG. 6 shows a SDS-PAGE gel loaded with the following samples: Lane 1 to 3: Three independent co-transfections of OA chain and OB chain; Lane 4: empty; Lane 5: co-transfection of WT long chain and short chain as a control. Lane 1 through 3 show substantially pure long/short chain heterodimer antibody, suggesting that the high purity production of OA and OB heterodimer is consistent.

Figure 7:
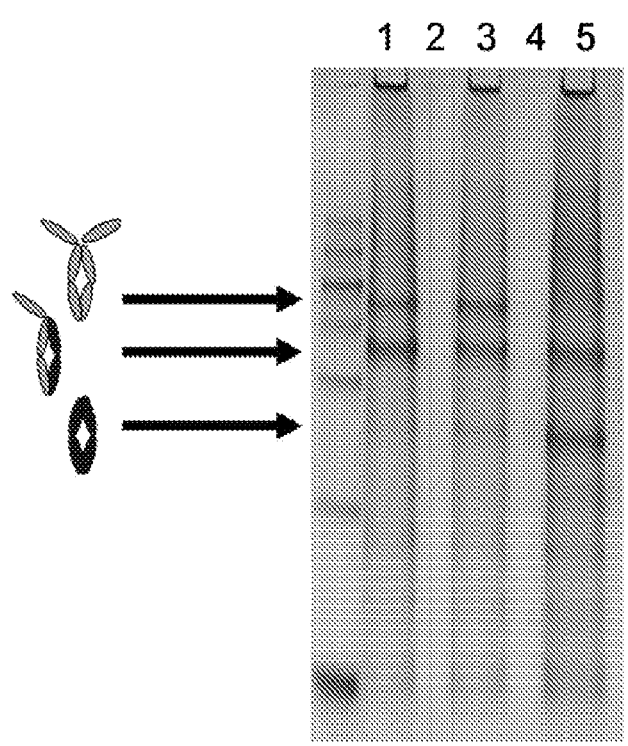
FIG. 7 shows a SDS-PAGE gel loaded with various samples. Lane M: Marker; Lane 1: Co-transfection of OG and OH chains; Lane 2: Empty; Lane 3: Co-transfection of OI and OJ chains; Lane 4: Empty; Lane 5: Co-transfection of OM and ON chains.

FIG. 7 is a SDS-PAGE gel analysis of following samples: Lane 1: Co-transfection of OG chain and OH chain; lane 2: empty; Lane 3: Co-transfection of OI chain and OJ chain; Lane 4: empty; Lane 5: Co-transfection of OM chain and ON chain. Amino acid mutations in each chain are disclosed in Example 2. In addition to heterodimer band in the middle, all three combinations have at least one homodimer band. Lane 1 and 3 have long chain homodimer band (top), whereas lane 5 has a short chain homodimer band (bottom). It suggests that the ratio between long chain and short chain needs to be adjusted (other than 1:1 ratio, such as 1:2 or 2:1 is needed) to maximize the yield of heterodimer band. More OH is needed in lane 1, more OJ is needed in lane 3 and more OM is required in lane 5.

Example 4: Single Step Purification Provides Highly Purified Antibodies

FIG. 8 illustrates the principle of the single step purification of the antibodies. Purification of Fc containing heterodimer bi-specific or multi-specific antibody can be accomplished by using methods known in the art. To achieve high purity of bi-specific or multi-specific antibody products after protein purification process, several known arts had intentionally introduced amino acid mutations (for example, H435R, or Y436F) to one of the two chains in Fc heterodimer to reduce or eliminate its binding activity to Protein A. Those methods were described in US2014/0348839 (MedImmune), WO 2010/151792, US20140248664 (Regeneron), PEGS2015 GBR1302 poster (Glenmark). Such modifications in heterodimer Fc had left only one chain in the Fc heterodimer binding to Protein A. As a result, this kind of heterodimer has weaker binding to Protein A compared to wild type homodimer, thus can be eluted at higher pH (between pH4.0 and 5.0), whereas normal Fc homodimer can only be eluted at pH 2.8 to pH3.0.

In the present invention, co-transfection of mutant OA and OB into HEK293 cells can produce high yield of heterodimer (above 95%) as showed in FIGS. 3, 4 and 6. Coincidently, Mutant OA had retained its Protein A binding activity (as demonstrated in FIG. 3 lane 7; FIG. 4 lane 1 and FIG. 5 lane 1), while mutant OB lost almost all its Protein A binding (as demonstrated in FIG. 3 lane 8; FIG. 4 lane 2 and FIG. 5 lane 2). Thus, the purification process described above can be easily applied to OA/OB heterodimer purification. OA/OB heterodimer purification strategy was illustrated in FIG. 8.

In one embodiment, OA and OB co-transfected cell culture supernatant was harvested and applied to protein A column. Because OB lost protein A binding activity, its homodimer, if there is any, will pass through the column or be washed away by wash step. Only OA/OB heterodimer was eluted from column at pH 4.2 (20 mM Na Citrate, 1M NaCl, pH 4.2). OA homodimer will remain on the column at this pH. Using this single purification step, the OA/OB heterodimer can be purified to high purity.

Figure 9:
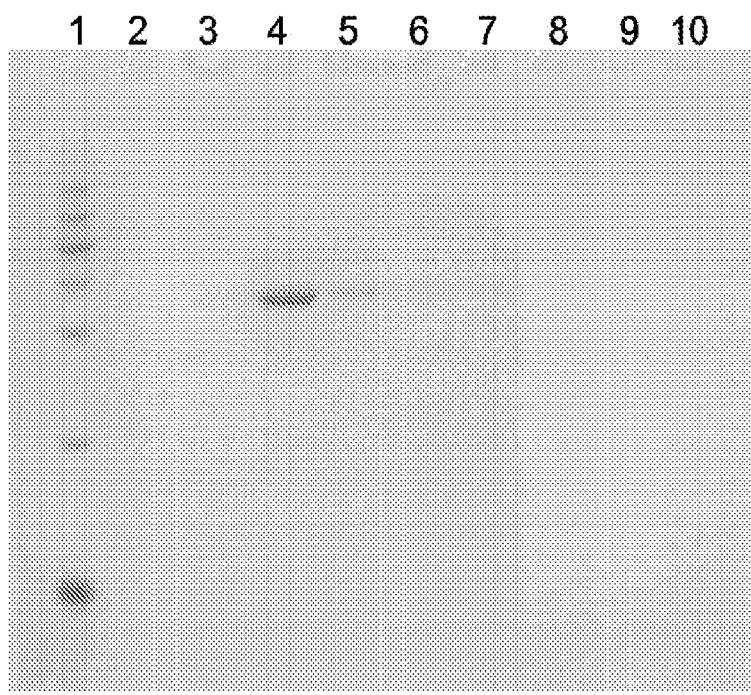
FIG. 9 shows a OA and OB heterodimer purification result using a Protein A column. OA and OB cotransfection sample was loaded to a Protein A column. After washing, the heterodimer product was eluted first at pH 4.0, and then eluted at pH 2.8. Lane 2 to 6 are pH 4.0 eluted fractions, and lane 7 to 10 are pH 2.8 eluted fractions. OA and OB heterodimer can be eluted at pH 4.0 as shown in lane 4 and 5.

The OA and OB heterodimer purification property is illustrated in FIG. 9. OA and OB cotransfection sample was loaded to a protein A column. After washing, the heterodimer product was eluted first at pH 4.0, and then eluted at pH 2.8. Lane 2 to 6 are pH 4.0 eluted fractions, and lane 7 to 10 are pH 2.8 eluted fractions. OA and OB heterodimer can be eluted at pH 4.0 as shown in lane 4 and 5.

Figure 10:
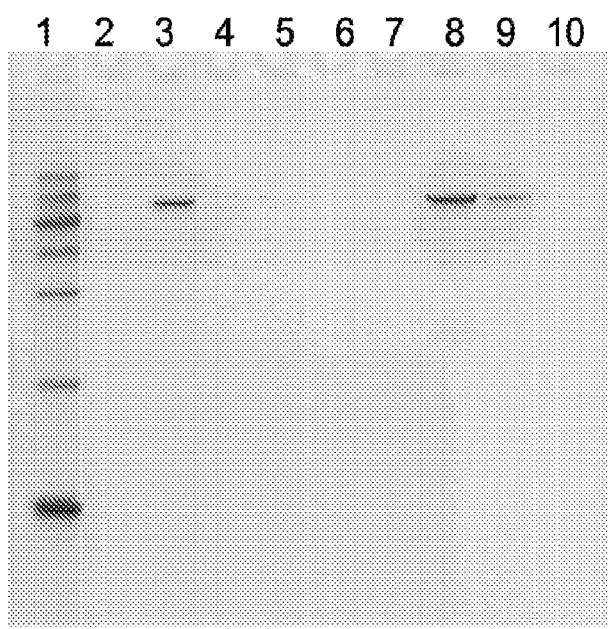
FIG. 10 shows a SDS-PAGE analysis of two purified bispecific antibody products. Lane 1 is molecular marker; Lane 2 to 6 are eluted fractions of the first bispecific antibody product Her2×CD3.1 (heterodimer of Anti-Her2 and Anti-CD3.1). Lane 7 to 10 are eluted fractions of the second bispecific antibody product Her2×CD3.2 (heterodimer of Anti-Her2 and Anti-CD3.2).

To demonstrate that OA and OB heterodimer facilitates a bispecific antibody formation, an anti-Her2 scFv derived from Herceptin VL and VH was fused in frame with OB fragment to generate Anti-Her2-OB using standard molecular cloning method. In addition, two anti-CD3 scFvs derived from two different anti-CD3 murine antibody VL and VH were fused in frame with OA Fc fragment (without CH1 region) to generate Anti-CD3.1-OA and Anti-CD3.2-OA using standard molecular cloning method. Two bispecific antibodies were generated by co-transfection of Anti-Her2-OB together with either Anti-CD3.1-OA or Anti-CD3.2-OA into HEK 293 cells using 293fectin from Life Technologies. Purified bispecific antibody products are illustrated in FIG. 10. Lane 1 is molecular marker; Lane 2 to 6 are eluted fractions of the first bispecific antibody product Her2×CD3.1 (heterodimer of Anti-Her2 and Anti-CD3.1). Lane 7 to 10 are eluted fractions of the second bispecific antibody product Her2×CD3.2 (heterodimer of Anti-Her2 and Anti-CD3.2).

Figure 11:
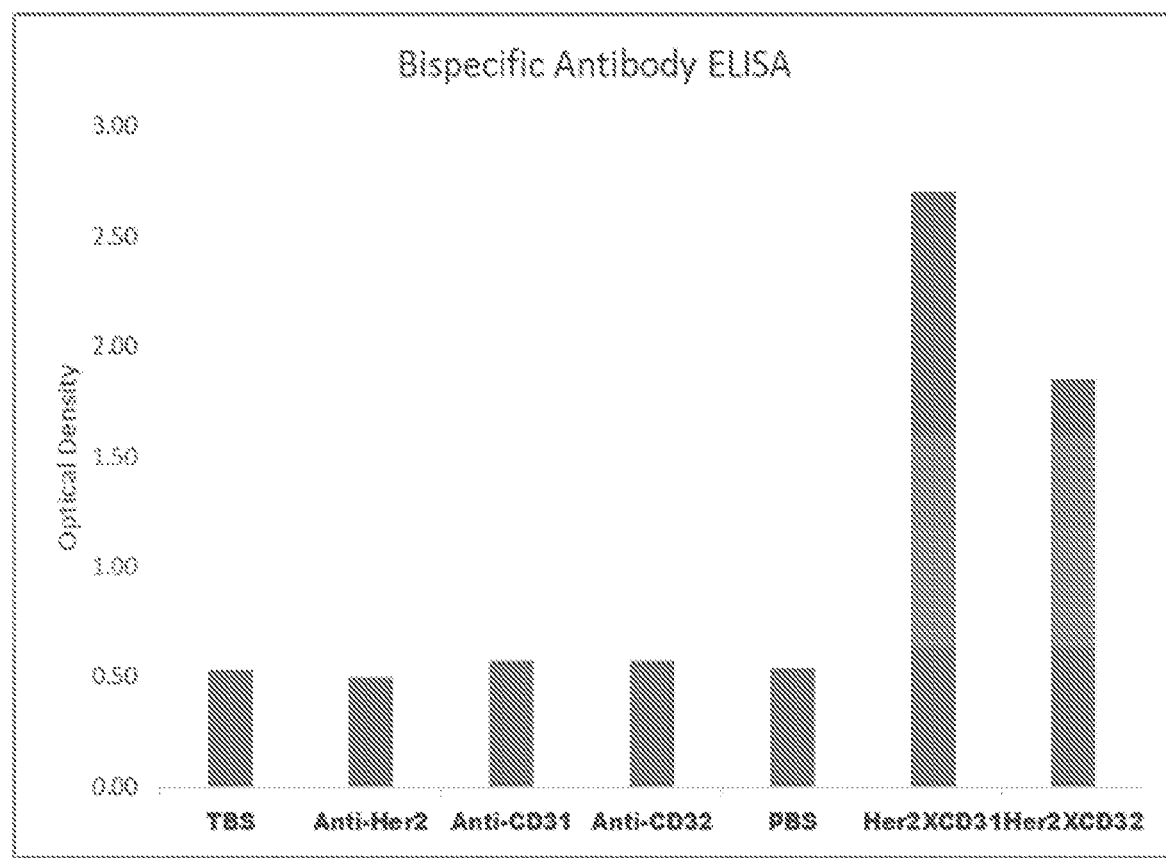
FIG. 11 shows a dual specific ELISA binding result. TBS and PBS are buffer controls. Anti-Her2 is a scFv derived from Herceptin fused to OA fragment. Anti-CD3.1 and Anti-CD3.2 are two scFvs derived from two different CD3 antibodies fused to OA fragment. Her2×CD3.1 is Anti-Her2-OB and Anti-CD3.1-OA heterodimer. Her2×CD3.2 is Anti-Her2-OB and Anti-CD3.2-OA heterodimer. The result indicated that only two heterodimer showed dual specific binding activity. Other single binding agents didn't show any dual specific binding activity.

To confirm the dual specific binding activity of those bispecific antibodies, a dual specific binding ELISA assay was carried out. A ELISA plate was coated with 2 µg/mL of human CD3 and blocked with 1% BSA blocker. Bispecific antibody samples and control samples were added to the plate and incubated for 1 hour at room temperature. After washing, a Her2 antigen (2 ng/mL) was added to the plate and incubated for 2 hours. After that a standard anti-Her2 ELISA was performed by using Human ErbB2 (Her2) ELISA kit from Thermo Scientific. The ELISA result was illustrated in FIG. 11. TBS and PBS are buffer controls. Anti-Her2 is a scFv derived from Herceptin fused to OA fragment. Anti-CD3.1 and Anti-CD3.2 are two scFvs derived from two different CD3 antibodies fused to OA fragment. Her2×CD3.1 is Anti-Her2-OB and Anti-CD3.1-OA heterodimer. Her2×CD3.2 is Anti-Her2-OB and Anti-CD3.2-OA heterodimer. The result indicated that only two bispecific antibodies showed dual specific binding activity. Other single specific agents failed to show any dual specific binding activity.

Although this invention has been described with a certain degree of particularity, it is to be understood that the present disclosure has been made only by way of illustration and that numerous changes in the details of construction and arrangement of parts may be resorted to without departing from the spirit and the scope of the invention.

Appendix Sequence listing

SEQ ID NO 1
TYPE: Protein (H1)
ORGANISM: Artificial sequence
Ser Asp Lys Thr Glu Pro Cys Gly Glu Cys Pro Ala Pro SEQ ID NO 2
TYPE: DNA
ORGANISM: Artificial Sequence
5'-TCT GAC AAA ACT GAA CCC TGC GGA GAA TGC CCA GCA CCT-3'

SEQ ID NO 3
TYPE: Protein (H2)
ORGANISM: Artificial sequence
Asp Lys Thr His Arg Cys Lys Ser Cys Pro Ala Pro SEQ ID NO 4
TYPE: DNA
ORGANISM: Artificial Sequence
5'-GAC AAA ACT CAC CGA TGC AAA TCC TGC CCA GCA CCT-3'

SEQ ID NO 5
TYPE: Protein (OA)
ORGANISM: Artificial Sequence
Tyr Lys Thr Thr Lys Lys Lys Leu Asp Ser Asp SEQ ID NO 6
TYPE: DNA
ORGANISM: Artificial Sequence
5'-TAC AAG ACC ACG AAG AAG AAG CTG GAC TCC GAC-3'

SEQ ID NO 7
TYPE: Protein (OB)
ORGANISM: Artificial Sequence
Tyr Lys Thr Asp Asp Asp Val Leu Asp Ser Asp SEQ ID NO 8
TYPE: DNA
ORGANISM: Artificial Sequence
5'-TAC AAG ACC GAT GAC GAT GTG CTG GAC TCC GAC-3'

SEQ ID NO 9
TYPE: Protein (OC)
ORGANISM: Artificial Sequence
Tyr Lys Thr Thr Lys Lys Cys Leu Asp Ser Asp SEQ ID NO 10
TYPE: DNA
ORGANISM: Artificial Sequence
5'-TAC AAG ACC ACG AAG AAG TGC CTG GAC TCC GAC-3'

SEQ ID NO 11
TYPE: Protein (OD)
ORGANISM: Artificial Sequence
Tyr Lys Thr Cys Asp Asp Val Leu Asp Ser Asp SEQ ID NO 12
TYPE: DNA
ORGANISM: Artificial Sequence
5'-TAC AAG ACC TGC GAC GAT GTG CTG GAC TCC GAC-3'

SEQ ID NO 13
TYPE: Protein (OG)
ORGANISM: Artificial Sequence
Tyr Lys Thr Thr Arg Arg Arg Leu Asp Ser Asp SEQ ID NO 14
TYPE: DNA
ORGANISM: Artificial Sequence
5'-TAC AAG ACC ACG AGA CGA AGG CTG GAC TCC GAC-3'

SEQ ID NO 15
TYPE: Protein (OH)
ORGANISM: Artificial Sequence
Asn Tyr Lys Thr Glu Glu Glu Val Leu Asp Ser SEQ ID NO 16
TYPE: DNA
ORGANISM: Artificial Sequence
5'-AAC TAC AAG ACC GAA GAG GAA GTG CTG GAC TCC-3'

SEQ ID NO 17
TYPE: Protein (OI)
ORGANISM: Artificial Sequence
Asn Asn Tyr Lys Lys Lys Lys Pro Val Leu Asp SEQ ID NO 18
TYPE: DNA
ORGANISM: Artificial Sequence
5'-AAC AAC TAC AAG AAG AAG AAG CCC GTG CTG GAC-3'

SEQ ID NO 19
TYPE: Protein (OJ)
ORGANISM: Artificial Sequence
Lys Thr Thr Pro Asp Asp Asp Asp Ser Asp Gly SEQ ID NO 20
TYPE: DNA
ORGANISM: Artificial Sequence
5'-AAG ACC ACG CCT GAC GAT GAC GAC TCC GAC GGC-3'

SEQ ID NO 21
TYPE: Protein (OM)
ORGANISM: Artificial Sequence
Asn Tyr Lys Thr Lys Lys Lys Val Leu Asp Ser SEQ ID NO 22
TYPE: DNA
ORGANISM: Artificial Sequence
5'-ACC TAC AAG ACC AAG AAA AAG GTG CTG GAC TCC-3'

SEQ ID NO 23
TYPE: Protein (ON)
ORGANISM: Artificial Sequence
Tyr Lys Thr Thr Asp Asp Asp Leu Asp Ser Asp SEQ ID NO 24
TYPE: DNA
ORGANISM: Artificial Sequence
5'-TAC AAG ACC ACG GAT GAC GAC CTG GAC TCC GAC-3'

SEQ ID NO 25
TYPE: Protein (OP)
ORGANISM: Artificial Sequence
Lys Thr Thr Pro Lys Lys Lys Asp Ser Asp Gly SEQ ID NO 26
TYPE: DNA
ORGANISM: Artificial Sequence
5'-AAG ACC ACG CCT AAG AAA AAG GAC TCC GAC GGC-3'

SEQ ID NO 27
TYPE: Protein (OQ)
ORGANISM: Artificial Sequence
Asn Asn Tyr Lys Asp Asp Asp Pro Val Leu Asp SEQ ID NO 28
TYPE: DNA
ORGANISM: Artificial Sequence
5'-AAC AAC TAC AAG GAC GAC GAC CCC GTG CTG GAC-3'

SEQ ID NO 29 (EPC)
TYPE: Protein
ORGANISM: Artificial Sequence
Asp Gly Ser Phe Glu Leu Glu Ser Glu Leu Thr Val Asp SEQ ID NO 30
TYPE: DNA
ORGANISM: Artificial Sequence
5'-GAC GGC TCC TTC GAA CTC GAA AGC GAA CTC ACC GTG GAC-3'

Appendix Sequence listing

SEQ ID NO 31 (FPC)
TYPE: Protein
ORGANISM: Artificial Sequence
Asp Gly Ser Phe Lys Leu Lys Ser Lys Leu Thr SEQ ID NO 32
TYPE: DNA
ORGANISM: Artificial Sequence
5'-GAC GGC TCC TTC AAA CTC AAG AGC AAG CTC ACC-3'

SEQ ID NO 33 (OS)
TYPE: Protein
ORGANISM: Artificial Sequence
Thr Leu Pro Pro Asp Asp Glu Glu Met Thr SEQ ID NO 34 (OS)
TYPE: DNA
ORGANISM: Artificial Sequence
5'-ACC CTG CCC CCA GAC GAT GAG GAG ATG ACC-3'

SEQ ID NO 35 (OT)
TYPE: Protein
ORGANISM: Artificial Sequence
Arg Glu Pro Gln Lys Lys Lys Leu Pro Pro Ser SEQ ID NO 36 (OT)
TYPE: DNA
ORGANISM: Artificial Sequence
5'-CGA GAA CCA CAG AAG AAG AAG CTG CCC CCA TCC-3'

What is claimed is:

1. An isolated polypeptide comprising: a CH3 domain, said CH3 domain comprising an amino acid sequence selected from the group consisting of SEQ ID NO:1, 3, 3, 5, 7, 9, 11, 13, 15, 17, 21, 23, 27, 27, 29, 31, 33 and 35.

2. A multispecific heterodimeric antibody comprising: a first immunoglobulin heavy chain comprising a first CH3 domain and a second immunoglobulin heavy chain comprising a second CH3 domain, wherein the first immunoglobulin heavy chain comprising the first CH3 domain has an amino acid sequence selected from the group consisting of SEQ ID No 3, 5, 9, 13, 17, 21, 25, 31, 35, and wherein the second immunoglobulin heavy chain comprising the second CH3 domain has an amino acid sequence selected from the group consisting of SEQ ID No 1, 7, 11, 15, 19, 23, 27, 29, 33.

3. The multispecific heterodimeric antibody of claim 2, wherein a first Fc region has positively charged amino acid substitutions and retains Protein A binding activity; wherein a second Fc region has negatively charged amino acid substitutions and has an altered or significantly reduced protein A binding affinity.

4. The multispecific heterodimeric antibody of claim 2, wherein the multispecific heterodimeric antibody presents a reduced Protein A binding affinity compared to wild type monoclonal antibody, such that the multispecific heterodimeric antibody can be eluted out from Protein A columns at pH 4.0 rather than pH 3.0, due to that only one of the Fc regions within the multispecific heterodimeric antibody retains Protein A binding activity.

5. The multispecific heterodimeric antibody of claim 2, wherein the first immunoglobulin heavy chain and the second immunoglobulin heavy chain further comprise one or two binding domains, selected from the group consisting of: Fab, ScFv, monoclonal antibody, monovalent antibody, bispecific antibody, multi-specific antibody, antibody drug conjugate, monobody, diabody, nanobody, probody, enzymatic domain, ligand, receptor fusion protein, and mini-binding domain.

6. The multispecific heterodimeric antibody of claim 2, wherein the multispecific heterodimeric antibody is human or humanized IgG, IgA, IgM, IgE or IgD.

7. The multispecific heterodimeric antibody of claim 2, wherein the multispecific heterodimeric antibody is human or humanized IgG1, IgG2, IgG3, or IgG4.

8. An antibody comprising: a first immunoglobulin heavy chain and a second immunoglobulin heavy chain, wherein the first immunoglobulin heavy chain comprises one of the following triple amino acid substitutions (P395K, P396K, V397K), (P395K, P396K, V397C) or (P395R, P396R, V397R), wherein the numbering is according to the EU numbering scheme; and the second immunoglobulin heavy chain comprises one of the following triple amino acid substitutions (T394D, P395D, P396D), (T394C, P395D, P396D) or (T394E, P395E, P396E), wherein the numbering is according to the EU numbering scheme, and vice versa.

9. A composition comprising: the multispecific heterodimeric antibody of claim 2 and a pharmaceutically acceptable carrier.

10. The isolated polypeptide of claim 1, wherein the isolated polypeptide is conjugated to a drug or a detectable label.

11. The multispecific heterodimeric antibody of claim 2, wherein the multispecific heterodimeric antibody is conjugated to a drug or a detectable label.

12. The multispecific heterodimeric antibody of claim 2, wherein the first CH3 domain comprises the amino acid sequence according to SEQ ID NO: 5 (OA) or SEQ ID NO: 9 (OC), and the second CH3 domain comprises the amino acid sequence according to SEQ ID NO:7 (OB) or SEQ ID NO: 11 (OD).

* * * * *